United States Patent [19]

Mahant

[11] Patent Number: 5,589,328
[45] Date of Patent: Dec. 31, 1996

[54] CHEMILUMINESCENCE ASSAYS BASED ON INDOXYL SUBSTRATES, THIOINDOXYL SUBSTRATES AND OTHER SUBSTRATES

[76] Inventor: Vijay K. Mahant, 5669 Amaya Dr., #367, La Mesa, Calif. 91942

[21] Appl. No.: 404,545

[22] Filed: Mar. 15, 1995

Related U.S. Application Data

[63] Continuation-in-part of Ser. No. 286,697, Aug. 4, 1994, abandoned.

[51] Int. Cl.$^6$ .............................. C12Q 1/00; C12Q 1/34; C12Q 1/44
[52] U.S. Cl. .................................. 435/4; 435/18; 435/19
[58] Field of Search .................................. 435/4, 18, 19, 435/21, 810; 548/484

[56] References Cited

U.S. PATENT DOCUMENTS

| | | | |
|---|---|---|---|
| 3,867,366 | 2/1975 | Rubenstein et al. | 260/121 |
| 4,065,354 | 12/1977 | Ullman et al. | 195/63 |
| 4,423,143 | 12/1983 | Rubenstein et al. | 435/7 |
| 4,708,929 | 11/1987 | Henderson | 435/7 |
| 4,942,127 | 7/1990 | Wada et al. | 435/11 |
| 5,266,700 | 11/1993 | Langhals et al. | 546/140 |
| 5,273,901 | 12/1993 | Jacobson et al. | 435/243 |
| 5,274,087 | 12/1993 | Barnett et al. | 536/23.5 |
| 5,281,522 | 1/1994 | Senyei et al. | 435/7.9 |
| 5,294,541 | 3/1994 | Kaplan et al. | 435/29 |
| 5,316,906 | 5/1994 | Haugland et al. | 435/4 |
| 5,320,942 | 6/1994 | Quaranta et al. | 435/7.23 |
| 5,322,769 | 6/1994 | Bolling et al. | 435/5 |
| 5,344,952 | 9/1994 | Mize et al. | 558/169 |

FOREIGN PATENT DOCUMENTS

| | | |
|---|---|---|
| 0091837 | 10/1983 | European Pat. Off. |
| 0243126 | 10/1987 | European Pat. Off. |
| 0408463 | 1/1991 | European Pat. Off. |
| 0476930A1 | 3/1992 | European Pat. Off. |
| 1128371 | 9/1968 | United Kingdom |
| 2233451 | 1/1991 | United Kingdom |
| 8800695 | 1/1988 | WIPO |
| 8909937 | 10/1989 | WIPO |
| 9000168 | 1/1990 | WIPO |

OTHER PUBLICATIONS

Alam and Cook, "Reporter Genes: Application to the Study of Mammalian Gene Transcription,"*Analytical Biochemistry* 188:245–254 (1990).

Blake, et al., "A Rapid, Sensitive Method for Detection of Alkaline Phosphatase–Conjugated Anti–antibody on Western Blots," *Analytical Biochemistry* 136:175–179 (1984).

BIO–RAD Lyphocheck Immunoassay controls, levels 1, 2, and 3, copy of page 17 from BIO–RAD catalog no date.

Bronstein, et al., "1,2–Dioxetanes: Novel Chemiluminescent Enzyme Substrates. Applications to Immunoassays," *Journal of Bioluminescence and Chemiluminescence* 4:99–111 (1989).

Bronstein, et al., "Chemiluminescent Assay of Alkaline Phosphatase Applied in an Ultrasensitive Enzyme Immunoassay of Thyrotropin," *Clin. Chem.* 35(7):1441–1446 (1989).

Bronstein and Voyta, "Chemiluminescent Detection of Herpes Simplex Virus 1 DNA in Blot and In–situ Hybridization Assays," *Clin. Chem.* 35(9):1856–1857 (1989).

Campbell, A. K., "Chemiluminescence Principles and Applications in Biology and Medicine," Ellis Horwood Ltd., Chichester (England) 1988, p. 47.

Campbell, A. K., "Fundamentals and Applied Aspects," *Bioluminescence and Chemiluminescence*, pp. 288–292, Proceedings of the 8th International Symposium on Bioluminescence and Chemiluminescence, Cambridge, Sep. 1994.

Clyne, et al., "A Rapid Chemiluminescent DNA Hybridization Assay for the Detection of *Chlamydia Trachomatis*," *Journal of Bioluminescence and Chemiluminescence* 4:357–366 (1989).

Cotson and Holt, "Studies in enzyme cytochemistry IV. Kinetics of aerial oxidation of indoxyl and some of its halogen derivatives," *Proceedings Royal Society (Series B)* 148:506–519 (1958).

de Melo, et al., "Horseradish Peroxidase–Catalyzed Aerobic Oxidation of Indole–3–Acetic Acid," *Archives of Biochemistry and Biophysics* 296(1):34–39 (1992).

Epstein, et al., "An Indigogenic Reaction for Alkaline Phosphates in Disk Electrophoresis," *The American Journal of Clinical Pathology* 48(5):530–534 (1967).

Escobar, et al., "Free Radicals and Excited Species in the Metabolism of Indole–3–Acetic Acid and its Ethyl Ester by Horseradish Peroxidase and by Neutrophils," *Photochemistry and Photobiology* 55(6):895–902 (1992).

Everse, et al. (Eds.), *Peroxidases in Chemistry and Biology*, vol. II, Chapter 2, "Biological Roles of Plant Peroxidases: Known and Potential Function," pp. 32–39 no date.

Ey and Ashman, "The Use of Alkaline Phosphatase–Conjugated Anti–Immunoglobulin with Immunoblots for Determining the Specificity of Monoclonal Antibodies to Protein Mixtures," *Methods in Enzymology* 121:497–509 (1986).

(List continued on next page.)

*Primary Examiner*—Ralph Gitomer
*Attorney, Agent, or Firm*—Robert D. Fish

[57] ABSTRACT

Chemiluminescence-based assays that detect or quantify enzymes that catalyze the hydrolysis of indoxyl esters are provided. The assays are based on the hydrolysis of indoxyl esters by enzymes of interest, such as alkaline phosphatase and others that are used as labels in immunoassays or nucleic acid hybridization reactions, or are present in body fluids. The assays include the steps of reacting a test sample with an indoxyl ester and, then, immediately or within a short time, typically less than about fifteen minutes, measuring the resulting chemiluminescence. The resulting chemiluminescence may be amplified by adding a chemiluminescence-amplifying reagent, such as horseradish peroxidase or lucigenin to the reaction.

20 Claims, No Drawings

OTHER PUBLICATIONS

Fowler, et al., "Labeling of Oligonucleotides With Horseradish Peroxidase and Detection Using Enhanced Chemiluminescence," *Technique-A Journal of Methods in Cell and Molecular Biology*, 2(5):261–267 (1990).

Franciand Vidal, "Coupling redox and anzymic reactions improves the sensitivity of the ELISA–spot assay," *Journal of Immunological Methods* 107:239–244 (1988).

Gershoni and Palade, "Protein Blotting: Principles and Applications," *Analytical Biochemistry* 131:1–15 (1983).

Hamilton, Robert G., "Production of Immunoassay Reagents,"*Immunoassay: A Practical Guide*, pp. 25–48 (1987).

Holt and Sadler, "Studies in Enzyme cytochemistry II. Synthesis of indigogenic substrates for esterases," *Proceedings Royal Society (Series B)* 148:481–494 (1958).

Kanofky, Jeffrey R., "Singlet Oxygen Production from the Peroxidase–catalyzed Oxidation of Indole–3–acetic Acid," *Journal of Biological Chemistry* 263(28):14171–14175 (1988).

Knecht and Dimond, "Visualization of Antigenic Proteins on Western Blots," *Analytical Biochemistry* 136:180–184 (1984).

Krylov and Chebotareva, "Peroxidase–catalyzed co–oxidation of indole–3 acetic acid and xanthene dyes in the absence of hydrogen peroxide," *FEBS Letters* 324(1):6–8 (1993).

Leary, et al., "Rapid and sensitive colorimetric method for visualizing biotin–labeled DNA probes hybridized to DNA or RNA immobilized on nitrocellulose: Bio–blots," *Proc. Natl. Acad. Sci. USA* 80:4045–4049 (1983).

Maeda, et al., "New Chemiluminescence Assay of Alkaline Phosphatase Using Lucigenin and its Application to Enzyme Immunoassay," *Bioluminescence and Chemiluminescence—Current Status*, pp. 356–360, Proceedings of the VIth International Symposium on Bioluminescence and Chemiluminescence, Cambridge, Sep. 1990.

Maeda, et al., "Chemiluminescent Assay of Alkaline Phosphatase Using Ascorbic Acid 2–Phosphate as Substrate and its Application to Chemiluminescent Enzyme Immunoassays," *Bioluminescence and Chemiluminescence*, pp. 119–122 no date.

Martin, et al., "Improved Chemiluminescent DNA Sequencing" *Biotechniques* 11:(1)110–113 (1991).

Cohn and Kaplan, "Blood Chemistry" *A Textbook of Clinical Pathology* pp. 257, 316 (1966).

Savage, et al., "Comparison of Simultaneous Azo Dye Coupling Methods and an Indiogenic Reaction for Alkaline Phosphatase in Polyacrylamide Disc Gels" *Stain Technology* 47(2):77–79 (1972).

Schaap, et al., "Chemiluminescent Substrates for Alkaline Phosphatase: Application to Ultrasensitive Enzyme–Linked Immunoassays and DNA Probes" *Clinical Chemistry* 35(9):1863–1864 (1989).

Sherry and Borgmann, "Enzyme–Immunoassay Techniques for the Detection of Atrazine in Water Samples: Evaluation of a Commercial Tube Based Assay" *Chemosphere* 26(12):2173–2184 (1993).

Albrecht, et al., "Chemiluminescent Enzyme Immunoassay of Prostate Specific Antigen (PSA) Based on Indoxyl Phosphate Substrate," *Bioluminescence and Chemiluminescence: Status Report*, pp. 317–319, Proceedings of the VIIth International Symposium on Bioluminescence and Chemiluminescence, Banff, Mar. 1993.

Sigma Chemical Company, *Biochemicals Organic Compounds for Research and Diagnostic Reagents*, p. 624 Product No. L 9756 (1994).

Snyder, et al., "Pattern Recognition Analysis of In Vivo Enzyme–Substrate Fluorescence Velocities in Microorganism Detection and Identification" *Applied and Environmental Microbiology* 1986:969–977 (1986).

Snyder, et al., "Rapid Characterization of Microorganisms by Induced Substrate Fluorescence: A Review" *Biotechnology Progress* 1(4):226–230 (1985).

Toyobo Co., Ltd. Biochemical Operations Department, *Toyobo Enzymes*, p. 97 no date.

Tsuji, et al., "Enzyme Immunoassays Monitored by Chemiluminescence Reactions of Lucigenin and NADH" *Luminescence Immunoassay and Molecular Applications*, Chapter 10, pp. 157–172 no date.

Tsuji, et al., "Chemiluminescent Enzyme Immunoassay—A Review" *Analytical Sciences* 5:497–506 (1989).

Valkirs and Barton, "ImmunoConcentration—New Format for Solid–Phase Immunoassays" *Clinical Chemistry* 31(9):1427–1431 (1985).

Wojtkowiak, et al., "A Sensitive Method for Staining Proteins Transferred to Nitrocellulose Sheets" *Analytical Biochemistry* 129:486–489 (1983).

Wolf, et al., "A New and Improved Histochemical Method for Sulfatase" *Laboratory Investigation* 15:1132 (1966).

CHEMILUMINESCENCE ASSAYS BASED ON INDOXYL SUBSTRATES, THIOINDOXYL SUBSTRATES AND OTHER SUBSTRATES

This application is a continuation-in-part of U.S. application Ser. No. 08/286,697 to Vijay Mahant, filed Aug. 4, 1994, entitled CHEMILUMINESCENCE ASSAYS BASED ON INDOXYL SUBSTRATES, now abandoned.

FIELD OF THE INVENTION

The present invention relates to chemiluminescence-based assays in which indoxyl, thioindoxyl (i.e., benzo[b]thiophene or benzo[b]furan ester esters or substrates are hydrolyzed by appropriate enzymes to produce chemiluminescent intermediate(s) or metabolites thereof. These hydrolysis reactions can be linked to a plethora of applications, including immunoassays, receptor assays, determination of leukocytes based on proteases, nucleic acid hybridization assays, reporter gene expression assays, and nucleic acid sequencing, in which enzyme activity is detected directly or indirectly. Uses for such assays include environmental, clinical, pharmaceutical, veterinary, food and oncological applications. These assays provide ultra-sensitivity and are clinically useful, for example, for analysis of body fluids, including serum, blood, saliva and urine.

BACKGROUND OF INVENTION

There is need for rapid, accurate and quantitative or qualitative determinations of substances in biological fluids and for compounds, particularly toxins and contaminants, in the environment and in food. For example, the presence of certain compounds, such as drugs, hormones, peptides, proteins and infectious organisms in blood, urine, saliva, vaginal secretions, dental plaque, cerebral spinal fluid and other biological and environmental samples has to be determined accurately and rapidly.

To provide such determinations, various assays have been developed by which biological and environmental substances can be detected and/or quantified and, if necessary, isolated. Such methods typically rely on specific binding reactions between the substance of interest and a compound specifically reactive with that substance. The resulting reaction or complex is measured or detected by a variety of known methods. The most commonly used methods employ a signal amplifying reagent or moiety of some type that is either already attached to one of the components of the complex, becomes part of the complex through further reaction or reacts with the complex to produce a detectable product. For example, nucleic acid probes may be labeled with biotin, which then binds to avidin or strepavidin. The biotin or avidin/strepavidin are labeled with reporter enzymes or radiolabels. Proteins are often detected with antibodies, which are labeled with reporter molecules, such as enzymes or radiolabels. The resulting complexes are measured by detecting the reporter molecule. Enzyme labels, such as alkaline phosphatase, are advantageous because of their relative stability, signal amplification, and because the labels are non-isotopic, the hazards and difficulties associated with handling and disposing radioisotopes are avoided. In diagnostic tests designed to be rapid and easy to use with moderate training in a doctor's office, clinic or environmental laboratory, the reporter molecule is often detected using colorimetric, fluorescent or chemiluminescent signals resulting from reaction of the enzyme label with its substrate.

Chemiluminescence

Molecular luminescence is the emission of electromagnetic (EM) radiation, including ultraviolet (UV), visible and infrared (IR) light, from a molecule as it returns from an excited state to a lower energy state, usually the ground state of the molecule. Luminescence includes radioluminescence, chemiluminescence, which includes bioluminescence, and photoluminescence, which includes fluorescence and phosphorescence. Coupling of luminescent labels or reactions to assays, such as immunoassays, has provided convenient and sensitive assays.

Chemiluminescence is produced when the excited product of an exoergic chemical process reverts to its ground state with the emission of light. Most chemiluminescent reactions require a step that involves oxidation of a reactant with molecular oxygen or its synthetic equivalent. Chemiluminescence is coupled to assays or used by using molecules, such as luminol, acridinium esters, isoluminol, lucigenin, dioxetanes and oxalate esters, that are capable of exhibiting chemiluminescence or transferring energy to an appropriate acceptor luminescent molecule or compound. The best known chemiluminescent reactions are those of acridinium esters, of dioxetane, of luminol/isoluminol and of lucigenin. For example, in the luminol and isoluminol chemiluminescent reactions, the key oxidative step involves reactions of hydrogen peroxide and aminophthalhydrazide in the presence of suitable catalysts.

Chemiluminescence assays are categorized on the basis of the labeling method. These assays rely on direct labels, such as acridinium esters, and indirect labels, such as enzymes, including alkaline phosphatase.

Enyzme-Based Assays

Enzyme-based assays are of particular interest herein. Enzyme-based assays have high intrinsic sensitivity, have relatively simple labeling procedures, and may be homogeneous and economical. Furthermore, enzymes may amplify a signal, and as a result, improve the sensitivity of an assay. Enzyme based assays are adaptable for use in conjunction with chemiluminescent, colorimetric, fluorimetric or electrochemical detection methods. In addition, enzyme detection methods overcome problems associated with the use of radioisotopes, such as health hazards and limited shelf-life. Assays of enzyme activity have numerous applications, including, enzyme immunoassays (EIA), assays that use nonisotopic nucleic acid probes; and nucleic acid sequencing reactions that use enzyme labels, such as alkaline phosphatase (AP).

Indoxyl ester derivatives, which serve as enzyme substrates, are chromogenic compounds that have been used for histochemical detection of endogenous enzymes, such as alkaline phosphatase, β-galactosidase, and β-glucosidase, esterase and sulfatase. In these assays, an appropriate indoxyl derivative is used as a substrate, which in the presence of the enzyme of interest is hydrolyzed into an intermediate indoxyl that in the presence of oxygen forms an indigo dye and hydrogen peroxide is produced. Previously the reaction was monitored spectrophotometrically by the formation of the indigo dye (see, e.g., Cotson et al. (1958) *Proc. Royal Soc. (Ser. B)* 148:506-519). Recently (see, e.g., EP 0 476 930 A1; Arakawa et al. (1991) *Anal. Biochem.* 199:238-242), a protocol for assaying the reaction by determining $H_2O_2$ has been described. The amount of hydrogen peroxide formed in this reaction is determined colorimetrically, fluorometrically, electrochemically, or chemiluminometrically using a chemiluminescent moiety, such as luminol or isoluminol in the presence of a catalyst, such as microperoxidase, and an oxidizing agent, $H_2O_2$ (see, EP 0 476 930 A1).

In particular, the reaction has been coupled to a reaction in which chemiluminescence is produced by reacting, in the presence of a peroxidase, the $H_2O_2$ produced in the hydrolysis reaction with a chemiluminescent moiety, such as isoluminol, as set forth in the following scheme (see, e.g., EP 0 476 930 A1):

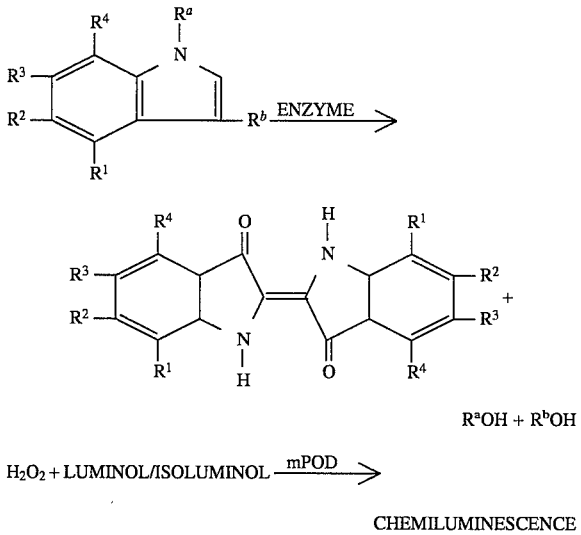

$$H_2O_2 + \text{LUMINOL/ISOLUMINOL} \xrightarrow{\text{mPOD}}$$

CHEMILUMINESCENCE

After the hydrolysis reaction goes to completion or as the reaction proceeds, the amount of hydrogen peroxide is determined in the second step by adding isoluminol and microperoxidase and measuring chemiluminescence Enzymes, such as alkaline phosphatase (ALP), β-galactosidase (β-gal), and β-glucosidase have been assayed by this method. Because the assay measures $H_2O_2$, the protocol, however, requires a sufficient incubation to permit stoichiometric formation of $H_2O_2$ so that the amount of chemiluminescence can be correlated with the amount of enzyme or substrate. It also requires the addition of other reagents, such as isoluminol, that are required for generation of chemiluminescence using $H_2O_2$. Also, the chemiluminescence-generating portion of the reaction, in which the resulting $H_2O_2$ reacts with luminol or its derivatives requires the use of a peroxidase, such as microperoxidase (MP) to catalyze the reaction. Microperoxidase, however, has limited stability, and the requisite reaction conditions for optimal quantum efficiency and faster kinetics (typically pH 11–13) may generate high background, thereby limiting sensitivity.

Other chemiluminescence reagents, such as lucigenin and lucigenin derivatives, such as acridinium esters, may also be added to generate chemiluminescence using $H_2O_2$. In these reactions, however, in order to generate sufficient chemiluminescence using $H_2O_2$, after addition of lucigenin and KOH or NaOH is added, or a lucigenin solution in KOH/NaOH is added in order to raise the pH. High pH is required when using lucigenin and $H_2O_2$ [see, e.g., Campbell, Chemiluminescence: Principles and Applications in Biology and Medicine, Ellis Horwood, Chichester, England 1988 pp 302–303; Maeda, et al. (1990) "New Chemiluminescence Assay of Alkaline Phosphatase Using Lucigenin and its Application to Enzyme Immunoassay," Bioluminescence and Chemiluminescence—Current Status, pp. 356–360, Proceedings of the VIth International Symposium on Bioluminescence and Chemiluminescence, Cambridge, September 1990; Maeda, et al. (1994) "Bioluminescence and Chemiluminescence, Fundamental and Applied Aspects", in Proceedings of the 8th International Symposium on Bioluminescence and Chemiluminescence, Cambridge, September 1994, pp 289–292]. Such changes in pH conditions may be deleterious to proteins, such as antibodies, antigens and enzymes, particularly in homogeneous assays. Also, lucigenin and/or its acridinium esters, when used to measure $H_2O_2$, provide a poor assay (A. Campbell, Chemiluminescence: Principles and Applications in Biology and Medicine, Ellis Horwood, Chichester 1988, p 302–303) because of high blanks and the conditions required to promote the reaction with $H_2O_2$.

Similar assays using indoxyl phosphate substrates and alkaline phosphatase for the determination of prostate specific antigen (PSA) (see, e.g., Albrecht et al. (1993) pages 316–319, in Bioluminescence and Chemiluminescence, Proceedings of the VIIth International Symp. on Bioluminescence and Chemiluminescence, Banff, March 1993, Eds. Szalay et al., John Wiley & Sons, New York) are also available. Following a 20 minute incubation of the substrate and alkaline phosphatase-labeled antigen, the reaction is stopped and mixed with oxalic acid, $H_2O_2$ and HCl to reduce the pH to about 1. A carobodimide is added to initiate the chemiluminescence reaction.

The hydrolysis of indoxyl esters can be catalyzed by numerous enzymes, such as alkaline phosphatase, depending upon the indoxyl substrate selected. The enzymes may be used as labels in numerous assays or may be present in body fluids or other samples of interest. Because of the versatility of assays that measure such enzymes, improved means for assessing this reaction are desirable. Therefore, it is an object herein to provide chemiluminescence-based enzyme assays of increased sensitivity, versatility, speed and reliability.

SUMMARY OF THE INVENTION

Chemiluminescence-based enzyme assays are provided herein. Chemiluminescence-based assays that detect or quantify enzymes that catalyze the hydrolysis of indoxyl esters, thioindoxyl esters (benzo[b]thiophene esters) or benzo[b]furan esters, particularly indoxyl esters, are provided. The assays are based on the hydrolysis of indoxyl esters by enzymes of interest, such as alkaline phosphatase and others that are used as labels in immunoassays or nucleic acid hybridization reactions, or are present in body fluids. The assays include the steps of reacting a test sample with an indoxyl ester and, then, immediately or within a short time, typically less than about fifteen minutes, measuring the resulting chemiluminescence. The resulting chemiluminescence may be amplified by adding a chemiluminescence enhancing reagent, such as horseradish peroxidase that catalytically amplifies the signal, or by adding an augmenting reagent that adds to the signal, such as lucigenin added without adjusting the pH of the reaction.

The assays herein are based on the discovery that chemiluminescence is generated by virtue of the hydrolysis reaction between the indoxyl ester, thioindoxyl ester (benzo[b]thiophene ester) or benzo[b]furan ester and enzyme. The assays are based on the hydrolysis of such esters, and do not require or measure the production of $H_2O_2$, which was measured in the prior assays using indoxyl esters. The assays do not require the use of added chemiluminescent generating systems, such as luminol or isoluminol and a peroxidase, or lucigenin in KOH, which is required for it to react with $H_2O_2$

[Maeda, et al. (1990) "Chemiluminescent Assay of Alkaline Phosphatase Using Ascorbic Acid 2-Phosphate as Substrate and its Application to Chemiluminescent Enzyme Immunoassays," *Bioluminescence and Chemiluminescence—Current Status*, pp. 119–122 and pp. 356–360, Proceedings of the VIth International Symposium on Bioluminescence and Chemiluminescence, Cambridge, September 1990].

In contrast, in the assays provided herein, chemiluminescence produced in the hydrolysis reaction is measured. This resulting chemiluminescence can be amplified by adding a chemiluminescence enhancing or augmenting reagent, such as an oxidizing enzyme or a catalyst, including horseradish peroxidase, or a reagent such as lucigenin under conditions, pH 7–11, in which it reacts with the superoxide anion and other reactive metabolites. Addition of a chemiluminescent generating system, such as luminol/isoluminol/peroxidase or the use of KOH with lucigenin for reaction with $H_2O_2$ is not required or used. The chemiluminescence amplifying reagent is one that reacts directly with the superoxide anion ($O_2^-$) or with another intermediate produced in the reaction to augment or enhance the resulting chemiluminescence.

Without being bound by any theory, the mechanism of indoxyl-(or thioindoxyl or benzo[b]furyl) chemiluminescence and peroxidase-catalyzed "enhanced" indoxyl-chemiluminescence production may involve dioxetane formation of the indoxyl intermediate or metabolite(s). The mechanism of "augmented" chemiluminescence, involves reaction of the superoxide anion generated in the hydrolysis reaction (see scheme, below) with lucigenin, thereby augmenting the chemiluminescence produced in the reaction.

The reaction is represented by the following scheme:

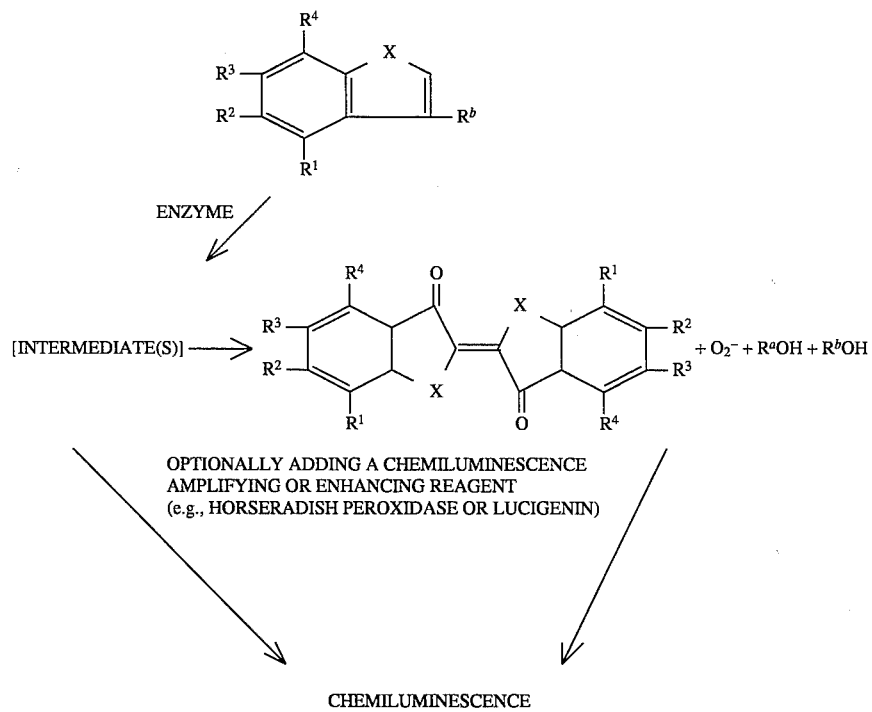

If a higher signal or sensitivity is desired the chemiluminescence produced in the reaction can be amplified. For example, peroxidase is added to catalytically enhance the signal; and lucigenin is added directly to the reaction, without any need to adjust the pH, to augment the resulting chemiluminescence. An amplifying reagent, such as a peroxidase, and an augmenting agent, such as lucigenin, may be included, and added either simultaneously, sequentially or intermittently.

Any indoxyl ester, thioindoxyl ester (benzo[b]thiophene ester) or benzo[b]furan ester that serves as a substrate for an enzyme of interest may be used. The preferred esters are 3-O-indoxyl esters, 3-O-thioindoxyl esters or 3-O-benzo[b]furan esters. The more preferred esters for use herein have the formula:

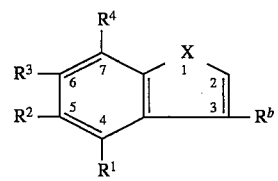

in which X is O, S, or preferably $NR_a$; $R^a$ is hydrogen or the acyl group of $R^b$, and is preferably hydrogen; and $R^b$ is any acyloxy group that can be hydrolyzed by an enzyme of interest. When $R^a$ is an acyl group, then it is preferably hydrolyzable by the same enzyme that hydrolyze $R^b$, otherwise, an additional enzymes may be required. Preferred acyl groups include, but are not limited to: phosphate, acetate, galactopyranosides, sulfate, glucuronate, glucopyranosides, fructopyranosides and mannopyranoside. Preferred acyl groups are also those derived from inorganic acids or simple organic acids.

$R^1$, $R^2$, $R^3$ and $R^4$, which are the same or different, are selected independently from hydrogen and small electrophilic moieties, which include halides, pseudohalides, haloalkyl, alkylamino, hydroxyl, alkyl, alkoxyalkyl, amino, and the like, in which the alkyl groups are preferably lower alkyl containing from 1 to 6 carbons, more preferably contain from 1 to 3 carbon atoms. In particular, $R^1$, $R^2$, $R^3$ and $R^4$ are selected from among cyano, amino, amino substituted with 1 or 2 methyl or ethyl groups, trihalomethyl, preferably trifluoromethyl, hydroxyl, halide, methyl, ethyl, methoxy and ethoxy. $R^1$, $R^2$, $R^3$ and $R^4$ are preferably hydrogen or halogen, and if halogen, are preferably Br or Cl.

In general, it is preferred that at least one of $R^1$, $R^2$, $R^3$ and $R^4$ is hydrogen. It is more preferred that at least two or three of $R^1$, $R^2$, $R^3$ and $R^4$ are hydrogen and one or two are halide. If two halides are present, then it is preferred that one is Cl and the other Br.

The most preferred compounds are 4-, 5- and 6-substituted 3-O-indoxyl esters. In compounds in which only one of $R^1$, $R^2$, $R^3$ and $R^4$ is not hydrogen, then it is preferably Br at the 5-position, or it is preferably Cl at the 6-position.

$R^a$ is preferably either hydrogen or the acyl group of $R^b$.

$R^b$ is selected such that it is hydrolyzed by the enzyme of interest. Thus, $R^b$ is virtually any such group, such as phosphate, acetate, amide, galactopyranoside, sulfate, glucuronate, glucopyranoside, fructopyranoside, mannopyranoside or any of the groups set forth above for $R^a$.

Other suitable indoxyl esters, thioindoxyl esters (benzo[b]thiophene esters) or benzo[b]furan esters may be identified by using them in a test assay in which a known amount of an enzyme that catalyses hydrolysis of the ester is mixed with the indoxyl ester, and chemiluminescence is measured immediately or within about 1 hour, preferably within seconds to about 30 minutes, more preferably within seconds to about 15 minutes, typically about 1 to about 5 or 10 minutes, after addition. If detectable chemiluminescence above background is produced, the ester is suitable for use in the assays herein. Thus, suitable indoxyl esters may be defined with reference to the ability to produce chemiluminescence above background upon reaction with a enzyme that hydrolyses the selected ester.

Kits for performing the chemiluminescence assays herein are also provided. In particular, kits for measuring enzymes that catalyze the hydrolysis of the esters are provided. These kits contain a first reagent containing the indoxyl ester; and a second reagent, containing a chemiluminescence amplifying reagent, such as horseradish peroxidase, lucigenin or any such reagent that reacts with the superoxide anion ($O_2^-$), a reactive metabolite and/or an intermediate in the reaction.

Methods for assessing enzyme activity and for identifying indoxyl esters, thioindoxyl esters (benzo[b]thiophene esters) or benzo[b]furan esters that are suitable substrates for the assays herein are also provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, a chemiluminescence amplifying reagent is a reagent that reacts with superoxide anion ($O_2^-$), or a reactive metabolite or with an intermediate product that is generated in the hydrolysis reaction between the indoxyl ester and enzyme of interest prior to stoichiometric conversion of the superoxide anion ($O_2^-$) to $H_2O_2$. These reagents include, but are not limited to, horseradish peroxidase, which reacts with a product generated in the hydrolysis reaction, pholasin, and lucigenin (dimethyl diacridinium nitrate), under conditions in which it reacts or detects superoxide [see, e.g., U.S. Pat. No. 5,294,541; see, also Campbell (1988) *Chemiluminescence: Principles and Applications in Biology and Medicine,* Ellis Horwood, Chichester, England, p. 336] and produces light in a reaction involving lucigenin, a dioxetane intermediate or metabolite, and/or other such reagents known to those of skill in the art or identified empirically. Other such reagents are any that react with the superoxide anion ($O_2^-$) or a reactive metabolite. These reagents can be identified by assays, such as those herein, that demonstrate the ability of the reagent to react with the superoxide anion [$O_2^-$; see, e.g., Examples]. Any reagent that reacts, either catalytically, such as horseradish peroxidase, to amplify chemiluminescence, or as a reactant with the superoxide anion ($O_2^-$) or a with a reactive metabolite to augment chemiluminescence may be used.

In particular, amplified chemiluminescence encompasses chemiluminescence that is "enhanced" or "augmented. For example, peroxidase-catalyzed "enhanced" indoxyl-chemiluminescence as used herein refers to the increase in indoxyl-chemiluminescence by a peroxidase, such as horseradish peroxidase as a result of catalysis or oxidation of an indoxyl metabolite(s) or an intermediate in a hydrolysis reactions provided herein. The chemiluminescence generated in the presence of a reagent, such as lucigenin, by virtue of reaction of the lucigenin or other such reagent with the superoxide anion or other reactive metabolite is herein referred to as augmented chemiluminescence.

Thus, amplified chemiluminescence as used herein refers to the amplification of the chemiluminescence as a result of chemical reaction between one or more enhancers or augmenters and one or more metabolites or intermediates produced in the reaction, for example, superoxide anion (radical) and an augmenter such as lucigenin. Superoxide anion and superoxide anion radical are used interchangeably.

As used herein, stoichiometric production of $H_2O_2$ refers to $H_2O_2$ produced in the hydrolysis reaction of the indolyl ester at the time at which substantially all intermediates in the production of $H_2O_2$ are converted to $H_2O_2$ or at a time when the amount of $H_2O_2$ is indicative of enzyme concentration. The reactions herein should be measured prior to such time, since they do not rely on $H_2O_2$ production.

As used herein, luminescence refers to the detectable EM radiation, generally, UV, IR or visible EM radiation that is produced when the excited product of an exoergic chemical process reverts to its ground state with the emission of light. Chemiluminescence is luminescence that results from a chemical reaction. Bioluminescence is chemiluminescence that results from a chemical reaction using biological molecules as substrates and/or enzymes.

As used herein, a chemiluminescent moiety is a molecule or compound that produces light in a chemical reaction under appropriate conditions.

As used herein, a reactive metabolite refers to any species, other than $H_2O_2$ that may be present in the hydrolysis reaction between the ester and enzyme. Such species include, but are not limited to intermediates, superoxide anion, and radical species.

As used herein, an analyte is any substance that is analyzed or assayed in the reaction of interest.

As used herein, indolyl is used interchangeably with indoxyl. Similarly thioindolyl is used interchangeably with thioindoxyl. It is also used interchangeably with benzo[b]thiophene or benzo[b]thiophenyl.

As used herein, a ligand refers to any compound, such as biotin, that binds reversibly and non-covalently to an anti-ligand, such as a specific binding protein, including avidin or strepavidin. Such ligands include growth factors, antibodies or fragments thereof, hormones, vitamins, and other types of proteins. An anti-ligand is a molecule that binds to such ligands.

The Assays

The assays provided herein are based on the discovery that an intermediate product of the hydrolysis reaction between an indoxyl ester, thioindoxyl ester (benzo[b]thiophene ester) or benzo[b]furan ester and an enzyme that catalyzes the hydrolysis produces chemiluminescence, which can be directly measured, or can be amplified by enhancing the signal or augmenting the signal. The resulting assays provide benefits compared to prior assays in that they provide: (1) elimination of the secondary incubation during which $O_2^-$ dismutates to $H_2O_2$, and (2) the substantially immediate or simultaneous addition of a chemiluminescence augmenting reagent to the hydrolysis reaction. In particular, these assays also provide: (1) versatility since the assays may be measured using (a) indoxyl-chemiluminescence, (b) peroxidase-catalyzed "enhanced" indoxyl-chemiluminescence without $H_2O_2$(2)/isoluminol, and/or (c) amplified chemiluminescence without altering the pH of the reaction or measuring or relying on $H_2O_2$; (2) the substantially immediate or simultaneous addition of a chemiluminescence amplifying reagent to the hydrolysis reaction, (3) shorter incubation (less than 15 minutes), and (4) higher sensitivity (see Examples) compared to the methods based on $H_2O_2$ determination.

Without being bound by any theory, it appears that the superoxide anion ($O_2^-$) or other intermediate, but not $H_2O_2$, is involved in the chemiluminescence generated in the instant assays, since, as demonstrated in the EXAMPLES, superoxide disumutase quenches the chemiluminescence. The chemiluminescence can be produced from the reaction of the esters, or using superoxide anion or other reactive intermediate or reactive metabolite. Thus, any chemiluminescence-amplifying reagent that reacts with superoxide anion ($O_2^-$) or reacts catalytically with an intermediate or reactive metabolite or superoxide anion to enhance or augment the chemiluminescence can be used in the instant assays. In contrast, the prior chemiluminescence indoxyl-based assays (see, e.g., EP 0 476 930 A1) rely on dismutation to $H_2O_2$.

Components of the Assays

Specimens and substrates

1. Indoxyl, thioindoxyl (benzo[b]thiophene), and benzo[b]furan ester substrates Substrates The preferred esters are 3-O-indoxyl esters, 3-O-benzo[b]furan and 3-O-thioindoxyl esters. The more preferred 3-O-indoxyl, 3-O-benzo[b]furan and 3-O-thioindoxyl esters for use herein have the formula:

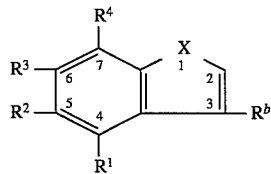

in which:

X is S, O or, preferably, $NR^a$, where $R^a$ is hydrogen, halogen, alkyl, alkoxy, alkoxyalkyl, aryl, aralkyl, aryloxy, hydroxl, carboxy, carboxy lower alkoxy, arylkoxycarbonyl, aryloxycarbonyl lower alkoxy, nitro, acyl, or lower acylamino groups, in which the lower alkyl groups contain from 1 to about 6 carbons, preferably 1–3 carbons, and the aryl groups preferably contain from about 4 to 7 members, preferably 5 or 6 members; $R^b$ is any acyloxy group or amide group linked to an amino group that can be hydrolyzed by an enzyme of interest, $R^a$ is hydrogen or the acyl group of $R^b$, and is preferably hydrogen. When $R^a$ is an acyl group, then it is preferably hydrolyzable by the same enzyme that hydrolyze $R^b$, otherwise, an additional enzymes may be required.

$R^b$ is selected such that it is hydrolyzed by the enzyme of interest. Thus, $R^b$ is virtually any such group, such as phosphate, acetate, galactopyranoside, sulfate, glucuronate, glucopyranoside, fructopyranoside, mannopyranoside or any of the groups set forth for $R^a$. $R^a$ is preferably either hydrogen or the acyl group of $R^b$. $R^b$ can also be of the formula (O-A-B) in which A is an amino acid, peptide residue, and B is a nitrogen protective group. Other preferred indolyl compounds are described, for example in U.S. Pat. No. 4,278,763 (see, also GB 1,128,371).

Preferred acyl groups include, but are not limited to: phosphate, acetate, galactopyranosides, sulfate, glucuronate, gluopyranosides, fructopyranosides and mannopyranoside. Preferred acyl groups are also those derived from inorganic acids or simple organic acids. In such instances in which the acyl group is preferably derived from phosphoric acid, phosphonic acid, sulfuric acid, sulfonic acid or carbonic acid.

$R^1$, $R^2$, $R^3$ and $R^4$, which are the same or different, are selected independently from hydrogen and small electrophilic moieties, which include halides, haloalkyl, alkylamino, hydroxyl, alkyl, alkoxyalkyl, amino, arylalkoxy, aralkoxycarbonylalkoxy, nitro, acylamino, and the like, in which the alkyl groups are preferably lower alkyl containing from 1 to 6 carbons, more preferably contain from 1 to 3 carbon atoms, and aryl groups preferably contain from 3–16, more preferably 3–10, more preferably 4–7, carbons.

In particular, $R^1$, $R^2$, $R^3$ and $R^4$ are selected from among cyano, amino, amino substituted with 1 or 2 methyl or ethyl groups, trihalomethyl, preferably trifluoromethyl, hydroxyl, halide, methyl, ethyl, methoxy and ethoxy. $R^1$, $R^2$, $R^3$ and $R^4$ are preferably hydrogen or halogen, and if halogen, are preferably Br or Cl.

In general it is preferred that at least one of $R^1$, $R^2$, $R^3$ and $R^4$ is hydrogen. It is more preferred that at least two or three of $R^1$, $R^2$, $R^3$ and $R^4$ are hydrogen and one or two are halide. If two halides are present, then it is preferred that one is Cl and the other Br; if one is present then it is preferably Br or Cl. The more preferred compounds are 3-O-indoxyl esters and 4-, 5- or 6-substituted 3-O-indoxyl esters most preferred. In compounds in which only one of $R^1$, $R^2$, $R^3$ and $R^4$ is not hydrogen, then it is preferably Br at the 5-position or Cl at the 6-position.

Indoxyl, thioindoxyl (benzo[b]thiophene) substrates, include, but are not limited to: indoxyl acetate, N-methyl indoxyl acetate; indoxyl-β-D-glucoside, indoxyl phosphate, N-methyl indoxyl acetate, N-methyl indoxyl myristate, 3-indoxyl phosphate and 3-indoxyl sulfate, and substituted derivatives thereof, including the corresponding thioindoxyl ester and benzo[b]furanyl ester.

Among the preferred indoxyl esters are: 3-indoxyl phosphate, 6-chloro-3-indoxyl phosphate; 6-chloro-3-indoxyl-β-D-galactopyranoside; 5-bromo-4-chloro-3-indolyl phosphate (BCIP) (see, e.g., Leary et al. (1983) *Proc. Natl. Acad. Sci.* 80:4045); 5-bromo-4-chloro-3-indolyl galactoside (X-Gal); several other "X-glycosides" that are similar to X-gal (see, e.g., Wolf et al. (1966) *Lab. Invest.* 15:1132); 5-bromo-4-chloro-3-indolyl phosphate for phosphatase;

5-bromo-4-chloro-3-indolyl galactoside (X-gal) for galactosidase; 5-bromo-4-chloro-3-indolyl sulfate for sulfatase; 3-indoxyl phosphate; 5-bromo-4-chloro-3-indolyl acetate for an acetate esterase; and 5-bromo-4-chloro-3-indolyl 2-acetamido-2-deoxy-β-D-glycopyranoside for N-acetylglycosaminidase. Other suitable indolyl substrates include indoxyl-amino esters, thioindolyl-amino esters, benzo[b]furanamino esters or peptide-derivatives thereof.

The indoxyl substrates, such as those for the phosphatases, sulfatases, galactosidases and some glycosidase enzymes, are known and commercially available, or may be synthesized by routine methods [see, e.g., U.S. Pat. Nos. 5.316.906 and 5,206,139]. Thioindoxyl esters (benzo[b]thiophene ester) and benzo[b]furan esters are also known [see, e.g., U.S. Pat. No. 4,278,763].

2. Enzymes

Any enzyme that catalyzes the hydrolysis of an indoxyl ester, preferably 3-O-indoxyl esters may be used herein. In particular, any esterase may be used as long as it hydrolyzes the indoxyl ester of interest. Such enzymes include, but are not limited to alkaline phosphatases, sulfatases, proteases and galactosidases. In particular, such enzymes include bacterial or intestinal alkaline phosphatase, β-galactosidase, β-glucuronidase, N-acetylcglucoseaminidase. Such enzymes are well known and may be isolated from readily available bacterial or tissue culture sources or may be purchased commercially. Such enzymes may be identified empirically, by selecting an indoxyl ester and testing selected enzymes for the ability to hydrolyze the ester.

3. Chemiluminescence Amplifying Reagents

Chemiluminescence amplifying reagents intended for use herein are any such reagent that reacts with superoxide anion ($O_2^-$) or an intermediate, such as a reactive metabolite or intermediate, other than, or in addition to, $H_2O_2$, generated in the hydrolysis reaction between the indoxyl ester and enzyme of interest. These reagents include, but are not limited to horseradish peroxidase, lucigenin (dimethyl diacridinium nitrate) added at the pH of the instant reactions (pH between about 7 and 11) without adjusting the pH of the reaction, which primarily and/or specifically detects superoxide anion (see, e.g., U.S. Pat. No. 5,294,541), an intermediate or reactive metabolite, and other such reagents. Other such reagents are any that react with the superoxide anion ($O_2^-$) or any reagent, such as horseradish peroxidase, that reacts with an intermediate that is generated in the hydrolysis reaction. These reagents react with or catalyze the reaction of an intermediate, and thereby enhance or augment the chemiluminescence. Suitable chemiluminescence amplifying reagents are known to those of skill in the art or can be identified empirically by testing a known reagent for the ability to generate chemiluminescence in the assays herein in which the reagent is added simultaneously or sequentially with the enzyme of interest or after the enzyme. Such reagents also can be identified by assays, such as those herein, that demonstrate the ability of the reagent to react with the superoxide anion ($O_2^-$) or or intermediates or other reactive metabolites [see, e.g., EXAMPLES].

Horseradish peroxidase or lucigenin, which is added without adjusting the pH of the hydrolysis reaction, are presently preferred. As shown herein, addition of lucigenin to the hydrolysis reaction, without adjusting the pH, augments the chemiluminescent signal. This augmentation, however, is quenched by addition of superoxide disumutase (SOD), which converts or dismutates superoxide anion to $H_2O_2$. This demonstrates that lucigenin is augmenting chemiluminescence produced in the reaction, but that the chemiluminescence is not produced by virtue of reaction of the lucigenin with $H_2O_2$. In contrast, as shown in the Examples, assays conducted according to the prior assays (see, e.g., EP 0 476 930 A1) are based on measurement of $H_2O_2$. Such chemiluminescence is not quenched by addition of SOD. Similarly in the prior assays, addition of SOD to reactions in which lucigenin is added after stoichiometric $H_2O_2$ production would not be expected to quench chemiluminescence.

Other suitable reagents include, but are not limited to: 7-dimethyl-amino-naphthalene-1,2-dicarbonic acid hydrazide and cypridina luciferin analogs, including 2-methyl-6-[p-methoxy phenyl]-3,7-dihyroimidazo[1,2- α] pyrazin-3-one, 2-methyl-6-phenyl]-3,7-dihydroimidazo[1, 2-β] pyrazin-3-one, 2-methyl-6-[p-[2-[sodium 3-carboxylato-4-(6-hydroxy-3-xanthenon-9-yl] phenyithioureylene] ethyleneoxy]phenyl]-3,7-dihydroimidazo[1,2-α] pyrazin-3-one and metal chelates.

Applications of the Assays

The assays herein have uses in human clinical, veterinary, and agricultural diagnostics, in the food industry in sterility and contamination testing of foods and beverages, and many other applications. The assays herein can be used in any method in which the activity of an enzyme that hydrolyzes an indoxyl, thioindoxyl (benzo[b]thiophene) or benzo[b] furan ester.

The methods herein can be applied to any application in which indoxyl esters and derivatives thereof have been used as substrates in spectrophotometric assays. For example, the conversion of indoxyls and substituted indoxyls into the corresponding indigo dye forms the basis for cytochemical staining methods for the localization of cellular enzymes [Holt et al. (1958) *Pro. Roy. Soc. B* 148:481]; indoxyls and derivatives have been used in the production of tissue stains to identify alkaline phosphatase activity [see, e.g, Cotson et al. (1958) *Proc. Roy. Soc. B.* 148:506]; bromo-chloro indoxyl phosphate has been used as a substrate for determining the specificity of monoclonal antibodies to protein mixtures in alkaline-phosphatase-conjugated antiimmunoglobulin in immunoblots [Ely et al. (1986) *Methods Enzymol.* 121:497]; bromo-chloro-indoxyl phosphate has been used for visualizing biotin-labeled DNA probes hybridized to DNA or RNA immobilized onto nitrocellulose [see, e.g., Leary et al. (1983) *Proc. Natl. Acad. Sci. USA* 80:4045]; and numerous other assays. Other chromogenic applications of the conversion of indoxyl compounds to indigo dye have included: an indigogenic reaction for alkaline and acid phosphatase histochemical demonstration in disk electrophoresis (see, Epstein et al. (1967) *Am. J. Clin. Pathol.* 48:530); the comparison of simultaneous azo-dye coupling methods and an indigogenic reaction for alkaline phosphatase in polyacrylamide disc gels [Savage et al. (1972) *Stain Technol.* 47:77]; protein blotting principles and applications [Gershoni et al. (1983) *Anal. Biochem.* 131:1]; a method for staining proteins transferred to nitrocellulose sheets [Wojtkowiak et al. (1983) *Anal. Biochem.* 129:486]; visualization of antigenic proteins on Western blots [D. A. Knecht, R. L. Dimond in Anal. Biochem. 1984, 136(1), 180]; a method for detection of alkaline phosphatase-conjugated anti-antibody on Western blots [Blake et al. (1984) *Anal. Biochem.* 136:175]; in solid phase immunoassays [Valkirs et al. (1985) *Clin. Chem.* 31:1427]; in ELISA-spot assays [Franci et al. (1988) *J. Immunol. Methods* 107:239]; and numerous other applications.

All of the preceding references rely exclusively on the spectral properties of bromo-chloro- indoxyl phosphate as a colorimetric substrate. For application in the methods herein, instead of monitoring the enzyme-catalyzed hydrolysis of the indoxyl ester to the indigo dye, however, the enzyme-catalyzed hydrolysis is monitored by detecting chemiluminescence of intermediates or reactive metabolites produced in the hydrolysis reaction as described herein.

The following applications of the methods herein are intended to be exemplary. Numerous other applications in which enzymes that react with indoxyl esters or compounds that can be labeled with such enzymes are known to those of skill in this art. Any application in which an enzyme that reacts with an indoxyl ester is a reactant, product or can be otherwise coupled, via an additional reaction or reactions may be practiced with the methods provided herein.

1. Human, veterinary and agricultural diagnostics using ligand binding assays The methods herein may be used in ligand binding assays for diagnostics. The ligand or the anti-ligand is labeled directly or indirectly with an enzyme such as, but not limited to, alkaline phosphatase (AP), B-D-galactosidase, sulfatase or B-D-glucuronidase. After appropriate incubation and separation, the appropriate substrate is added and the activity of the enzyme is measured by methods herein. The concentration of the unknown sample is determined from a standard-dose-response curve. Examples of ligand binding assay include immunoassays, protein binding assays, and nucleic acid hybridization assays.

(a) Immunoassays employing labeled antigen or labeled antibody

Enzyme labels are used in numerous immunoassays. For example, a number of heterogeneous immunoassays employing alkaline phosphatase have been reported [see, e.g., Bronstein et al. (1989) *Clin. Chem.* 35:1441–1446 and Schaap et al. (1989) *Clin. Chem.* 35:1863–1864]. Homogeneous assays employing B-galactosidase are also well known [see, e.g., U.S. Pat. No. 4,708,929].

Other immunoassays for identifying antigens of interest include: methods for diagnosing the presence of abnormal epithelial tissue using monoclonal antibodies to the A6B4 cell surface protein [see, e.g., U.S. Pat. No. 5,320,942]; methods for detecting fetal fibronectin [see, e.g., U.S. Pat. No. 5,281,522]. These reactions use a reagent, such as a biotin-conjugated goat anti-human immunoglobulin-specific antibody and alkaline phosphatase-conjugated rabbit anti-biotin specific antibody (see, e.g., U.S. Pat. No. 5,322,769). A substrate, such as 5-bromo-4-chloro-3-indolyl phosphate can be used in the methods herein and the activity or the alkaline phosphatase can be determined [see, e.g., Examples].

(b) Receptor assays employing labeled ligand or labeled receptor

Assays for receptors that use enzyme-labeled analytes are known. For example, asteroid is labeled with alkaline phosphatase and the appropriate receptor is used as and anti-ligand. After incubation and separation, substrate is added and chemiluminescence is measured (see, e.g., Hamilton et al. (1987) Chapter 2, pages 22–48 in *Immunoassay A Practical Guide,* Chan et al., eds, Academic Press, Inc. New York).

(c) Protein binding assays employing a labeled ligand or labeled anti-ligand

Protein binding assays (see, e.g., Hamilton et al. (1987) Chapter 2, pages 22–48 in *Immunoassay A Practical Guide,* Chan et al., eds, Academic Press, Inc. New York) may be practiced with the methods herein. Such assays include, but are not limited to (i) assays that use serum binding proteins, such as, but not limited to, thyroxine-binding globulin, transcortin, intrinsic factor (the gastric mucosa vitamin $B_{12}$ transport protein, and sex hormone-binding globulin; and (ii) assays involving cell surface and tissue receptors. The ligands for the binding proteins or receptors, or the binding proteins or receptors (i.e. the anti-ligand) are labeled with an appropriate enzyme, such as alkaline phosphatase, which can then be determined as described herein.

(d) Nucleic acid hybridization assays

Nucleic acids (i.e. DNA, RNA or analogs thereof) can be labeled with enzymes, such as alkaline phosphatase, that react with indoxyl esters. Also, nucleic acids and analogs thereof may be labeled with biotin, which binds to avidin or strepavidin conjugated with alkaline phosphatase. The labeled nucleic acids, which may be used as probes, may then be identified and quantified (see, e.g., Bronstein et al. (1989) *Clin. Chem.* 35(9):1856–1857, in which an oligonucleotide probe is labeled with alkaline phosphatase or with a ligand, such as biotin that binds to avidin or to streptavidin conjugated with alkaline phosphatase; see, also see, e.g., U.S. Pat. Nos. 5,316,906 and 5,274,087). Following hybridization, alkaline phosphatase is determined by the methods herein.

Also, expression of β-galactosidase is a marker detected in plaque assays (see, e.g., U.S. Pat. Nos. 5,281,522 and 5,273,901). A substrate, such as 5-bromo-4-chloro-3-indolyl-D-galactopyranoside can be used in the methods herein and used to detect and/or quantify β-galactosidase.

2. Environmental Applications and for Chemical Assays

The assays herein may be used to measure environmental compounds such as parathion, toluene, sulfamethazine, melathion and heptachlor using alkaline phosphatase labeled antigert or antibody (see, e.g., U.S. Pat. No. 5,266,700). Enzyme immunoassays have also been used to measure atrazine in water samples [see, Sherry et al. (1993) *Chemosphere* 226:2173–2184].

3. Pharmaceutical and Toxicological Applications

The assays may be used in drug design by assessing the effect of a drug on an enzyme such as alkaline phosphatase. For example, compounds, such as levamisole analogs, that inhibit particular forms of alkaline phosphatase [i.e. kidney, liver, tumor or placental forms of alkaline phosphatase; see, e.g., Biochemicals, Organic Compounds for Research and Diagnostic Reagents, SIGMA Chemical Company 1994 catalog], can be identified by the assays herein.

The assays may be used to screen for microbes and microbial contamination. The assays may be used to determine the purity of genetically engineered or produced enzymes, such as β-D-galactosidase. Identification and antimicrobial susceptibility tests can be performed on a suspension of a pure culture isolate. Substrates and other reagents for these pure culture tests are known to those of skill in the art [see, e.g., European Patent Application EP 091,837 A; Snyder et al. (1985) "Rapid Characterization of Microorganisms by Induced Substrate Fluorescence: A Review" *Biotechnology Progress* 1:226–230; Snyder, et al. "Pattern Recognition Analysis on In Vivo Enzyme Substrate Fluorescence Velocities in Microorganism Detection and Identification" *Appl. Environ. Microbiol.* 51:969–977]. For microbial identification, a culture suspension is added to solutions, each containing a different substrate, and incubated at an appropriate temperature. Multiple enzyme tests may be formatted into a panel of tests. Depending upon the type of microorganism, certain substrates will be cleaved by specific enzymes produced by the microorganism. For example, coliform bacteria produce the enzyme β-galactosidase; and *E. coli* bacteria produce the enzyme glucuronidase. Recognition of the specific enzymes that a particular microorganism produces permits identification of the pure culture isolate. Antimicrobial susceptibility patterns can be obtained by measuring a reduction in the amount of enzyme produced by a pure culture isolate in the presence of certain antimicrobial compounds. Reduction in the amount of enzyme produced by the pure culture isolate is directly related to the susceptibility of that microorganism to the antimicrobial.

*E. coli* β-galactosidase is inhibited by silver nitrate, p-chloromercuribenzoate and dimethylbenzylalkylammonium chloride [see, e.g., Toyobo Enzymes (catalog) Toyobo Co. LTD.]. The methods herein may be used in assays that monitor β-galactosidase inhibition, thereby detecting the presence of such inhibitors or toxicological compounds.

4. DNA Sequencing

Chemiluminescence DNA sequencing may be performed using the dideoxy method (see, e.g., Martin et al. (1991) *Improved Chemiluminescent DNA Sequencing Biotechniques* 11:110–113).

DNA sequencing reaction may also be detected by chemiluminescence using nylon membrane and hybridization of probes. that are either labelled with alkaline phosphatase or a ligand, such as biotin to which streptavidin-alkaline phosphatase conjugate is then added. After washing, the activity of alkaline phosphatase is measured by the methods herein.

5. Reporter Gene Assays

Reporter gene assays have numerous applications in which levels of expression of a gene operatively linked to an inducible promoter are measured. The most commonly described reporter gene assays use chloramphenicol acetyl transferase, β-galactosidase, luciferase, B-glucuronidase and secreted alkaline phosphatase (Alam, et al. (1990) *Anal. Biochem.* 188:245–254). Of interest herein are those assays in which an enzyme, such as β-galactosidase or alkaline phosphatase is expressed. The methods herein are used to detect and/or quantify such enzymes.

6. Diagnosis of Periodontal Diseases

Chemiluminescence assays for alkaline phosphatase in the diagnosis of human periodontal disease using aryl dioxetane phosphate are known, (see e.g., Ian et al. (1993) *Luminescence and Chemiluminescence Proceedings of the VIIth International Symposium on Bioluminescence and Chemiluminescence*, Banff, March 1993, Szalay et al. ed.). Increased alkaline phosphatase activity is correlated with periodontal disease. Accordingly, the methods herein may be used to measure alkaline phosphatase activity in saliva, gingival cervicular fluid and other fluids or tissues in the mouth.

7. Clinical Chemistry Diagnostics

Increased levels of alkaline phosphatase are associated with liver and bone diseases (see, e.g., Cohn et al. (1966) *Blood Chemistry in a Textbook of Clinical Pathology*, 7th Edition, S. E. Miller, Ed., Williams & Wikins, Baltimore, Md., page 316). Serum alkaline phosphatase activity may reach about ten to twelve and up to 25 times the upper limit of normal in hepatic obstruction and in Paget's Disease. A moderate increase in serum alkaline phosphatase occurs in osteomalacia, rickets, congestive heart failure and Fanconi's Syndrome, hyperthyroidism, intestinal disease and intra-abdominal bacterial infections.

Accordingly, serum may be sampled and tested for alkaline phosphatase according to the methods herein.

8. Food, Beverage and Sterility Testing

The methods herein may be used to test analytes in food and beverages. For example, vitamin B12 or antibiotics using a vitamin B12 or antibiotic-specific alkaline phosphatase-labelled antigen or antibody in an immunoassay.

Alkaline phosphatase and other bacterial enzymes (see, discussion above) may been used as a marker to check for sterility or degree of contamination, for example, in medical supplies and food. Bacteria produce enzymes such as β-galactosidase that can be quantified by the methods herein. As discussed above, coliform bacteria produce the enzyme β-galactosidase; and *E. coli* bacteria produce the enzyme glucuronidase.

9. Detection of Leukocytes

The methods herein may be used to detect leukocyte-specific proteases and thereby detect leukocytes in body fluids. Detection of leukocytes in body fluids has important applications, such as in the assessment of kidney or renal damage. These methods may be practiced using the thioinoxyl substrates [see, e.g., U.S. Pat. No. 4,278,763].

Kits and diagnostic systems

The assay systems herein may be provided in kit form that is useful for detecting the enzyme, cofactor, substrate, product, intermediate or reactive metabolite in a sample, such as a food, body fluid or tissue. All kits also include instructions for performing the assays.

In particular, kits for performing the chemiluminescence assays herein are also provided. In particular, kits for measuring enzymes that catalyze the hydrolysis of indoxyl esters are provided. These kits contain a first reagent containing the indoxyl ester; and a second reagent, containing a chemiluminescence amplifying reagent, such as horseradish peroxidase (but do not contain horseradish peroxidase and luminol/isoluminol), lucigenin added without adjusting the pH, or other such reagent. The kits may also include suitable ancillary reagents, such as the appropriate buffers, such as diethanolamine and borate buffer, at a pH appropriate for the reaction, typically between about 7 and about 11 or slightly higher, preferably 7 to 11 or 7 to 10.5 or 7.5 to 10, depending upon the enzyme. The kits may also include suitable ancillary supplies, such as microtiter plates, vials, labeled ligand or labeled anti-ligand, calibrator solutions, controls, wash solutions, solid-phase supports and the like.

The packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays.

Practice of the assays

The diagnostic tests provided herein include assays for enzymes that catalyze the hydrolysis of indoxyl esters. The enzymes may be used as labels in various immunoassays and DNA hybridization assays or in DNA sequencing reactions. The enzymes may be present in sampled body fluids and, thus, be used to detect and/or quantify the enzyme, such as alkaline phosphatase, which may be indicative of disease.

In practicing the assays herein, the test sample and indoxyl ester, which is selected for its ability to be hydrolyzed by the enzyme that is of interest and that may be present in the test sample, are mixed. Chemiluminescence is measured thereafter, typically immediately or within a few minutes (1 to about 15 minutes or preferably 1 to about 5 or 10 minutes). Alternatively, if amplifcation of the chemiluminescent signal is desired, a chemiluminescence-amplifying reagent, such as horseradish peroxidase or lucigenin, can be added to the reaction mixture. The chemiluminescence-amplifying reagent, can be added simultaneously with addition of the test sample or other reagent, or within a short period thereafter, typically less than one minute up to an hour, preferably between about 1 and 15 minutes. The time at which a chemiluminescence-amplifying reagent is added is preferably less than 10 minutes, can be less than about five minutes, less than about one minute or even simultaneously with one or more reagents. It can be added, particularly if the reagent is a peroxidase, up to one to two hours after commencement of the hydrolysis reaction. Chemiluminescence is measured immediately thereafter. The chemiluminescence-amplifying reagent is any such reagent that reacts with the superoxide anion ($O_2^-$) or with another reactive metabolite (other than $H_2O_2$) produced in the hydrolysis reaction, thereby increasing the chemiluminescence signal generated in the reaction.

The following examples are included for illustrative purposes only and are not intended to limit the scope of the invention.

EXAMPLE 1

Alkaline Phosphatase-Mediated Chemiluminescence of Indoxyl Phosphate Esters

A. Materials (1) Substrate solution (a) 3.5 mM 3-indoxyl phosphate, di-p- toluidine salt (DCL, Canada) in 0.1M diethanolamine buffer containing 2 mM $MgCl_2$, pH 10.

(b) 3.5 mM 3-indoxyl phosphate, di-(2-amino-2-methyl-1,3-propanediol salt (JBL, CA) in 0.1M diethanolamine buffer containing 2 mM $MgCl_2$, pH 10.

(c) 3.5 mM 5 bromo-4-chloro-3 indoxyl phosphate, mono- (p-toluidinium) salt (JBL, CA) in 0.1M diethanolamine buffer containing 2 mM $MgCl_2$, ph 10.

(d) 3.5 mM 6-chloro-3-indolyl phosphate, p-toluidine salt (Research Organics INC, OH)) in 0.1M diethanolamine buffer containing 2 mM $MgCl_2$, pH 10.

(2) Enzymes (a) Alkaline phosphatase (AP), (Biozyme Laboratories International, CA)

(b) Superoxide dismutase (Biozyme Laboratories International, CA)

B. Method (1) 10 μL of the sample solution (blank and alkaline phosphatase) was added to plastic tubes.

(2) 50 μL of each of the above substrate solution was injected using the AccuLyte luminometer (LTI, IL) into the sample tubes.

(3) Chemiluminescence was measured using the AccuLyte luminometer for 180 seconds.

C. Results

| | Relative Light Units (RLU) | |
|---|---|---|
| Substrate solution | Blank | Alkaline Phosphatase ($6.25 \times 10^{-15}$ moles) |
| (a) | 10,381 | 283,479 |
| (b) | 14,998 | 145,643 |
| (c) | 10,140 | 32,299 |
| (d) | 11,543 | 22,356 |

D. Discussion

The above results demonstrate that enzymatically catalyzed hydrolysis of the indoxyl esters produces chemiluminescence.

EXAMPLE 2

Effect of Superoxide Dismutase (SOD)

A. Materials (1) Substrate solution 3.5 mM 3-indoxyl phosphate, di-p- toluidine salt (DCL, Canada) in 0.1M diethanolamine buffer containing 2 mM $MgCl_2$, pH 10.

(2) Enzymes (a) Alkaline phosphatase (AP), (Biozyme Laboratories International, CA)

(b) Superoxide dismutase (SOD; Biozyme Laboratories International, CA).

B. Method (1) Pipet 10 μL of blank and $6.5 \times 10^{-15}$ moles alkaline phosphatase solution into plastic tubes.

(2) Pipet 10 μL of 58 mU of SOD or zero mU (blank) of SOD.

(3) Inject 50 μL of 3.5 mM 3-indoxyl phosphate, toluidine salt into the AccuLyte luminometer.

(4) Measure chemiluminescence for 180 seconds using the AccuLyte luminometer.

C. Results

| | Blank (−)no SOD | AP† (−)SOD | Blank (+)SOD | AP† (+)SOD |
|---|---|---|---|---|
| SOD | None (0) | None (0) | 58 mU | 58 mU |
| RLU* | 11,130 | 254,222 | 10,415 | 10,140 |

†$6.25 \times 10^{-15}$ moles AP
*RLU = relative light units

D. Discussion

These results demonstrate that chemiluminescence is quenched by the addition of SOD, which converts the superoxide anion into $H_2O_2$, thereby suggesting that the superoxide anion is involved in the production of chemiluminescence from the indoxyl intermediate or other reactive metabolite.

EXAMPLE 3

Peroxidase-Catalyzed Chemiluminescence of 3-Indoxyl Phosphate

Materials (1) Alkaline phosphatase (AP) solutions, $8.6 \times 10^{-15}$ mol/10 µL, $8.6 \times 10^{-17}$ mol/10 µL, and $8.6 \times 10^{-18}$ mol/10 µL, in 0.1M diethanolamine buffer containing 2 mM magnesium chloride ($MgCl_2$), pH 10.0, were prepared.

(2) Substrate solution was prepared by adding 10 µL of horseradish peroxidse (HRP; 2.5 units in 0.1M Tris, pH 7.8, containing 0.05% bovine serum albumin) to 100 µL of 3.5 mM 3-indoxyl phosphate, di-p-toludine salt (in 0.1M diethanolamine buffer, containing 2 mM $MgCl_2$, pH 10.0).

Methods

The alkaline phosphatase solution (10 µL) was introduced into a plastic tube. Substrate solution (20 µL) was added and chemiluminescence was measured in an OPTOCOMP1 (MGM) Luminometer for 20 second intervals for 20 intervals.

Results

| INTER-VAL | BLANK RLU | $8.6 \times 10^{-15}$ mol AP RLU | $8.6 \times 10^{-17}$ mol AP RLU | $8.6 \times 10^{-18}$ mol AP RLU |
| --- | --- | --- | --- | --- |
| 1 | 1078 | 232859 | 2419 | 1359 |
| 2 | 983 | 343331 | 2932 | 1265 |
| 3 | 964 | 345951 | 3854 | 1300 |
| 4 | 955 | 342039 | 4849 | 1353 |
| 5 | 952 | 329859 | 5843 | 1364 |
| 6 | 955 | 313922 | 6719 | 1407 |
| 7 | 945 | 296669 | 7377 | 1402 |
| 8 | 925 | 280091 | 7850 | 1440 |
| 9 | 934 | 264388 | 8238 | 1448 |
| 10 | 918 | 249550 | 8506 | 1447 |
| 11 | 925 | 235630 | 8684 | 1467 |
| 12 | 917 | 222530 | 8776 | 1464 |
| 13 | 891 | 209959 | 8717 | 1452 |
| 14 | 910 | 197605 | 8876 | 1430 |
| 15 | 898 | 187537 | 8855 | 1466 |
| 16 | 929 | 179204 | 8825 | 1458 |
| 17 | 906 | 172108 | 8787 | 1447 |
| 18 | 888 | 166390 | 8834 | 1447 |
| 19 | 894 | 160628 | 8784 | 1445 |
| 20 | 891 | 155792 | 8731 | 1439 |

EXAMPLE 4

Effect of Superoxide Dismutase on Peroxidase-Catalyzed Indoxyl Chemiluminescence Enhancement

Materials

Substrate solution containing 3-indoxyl phosphate toluidine salt (2.3 mM) in diethanolamine buffer (70 mM; $MgCl_2$ (2.0 mM); pH 10.0).

Methods

Substrate solution was added to 10 µL of alkaline phosphatase ($8.6 \times 10^{-15}$ mol) sample, and incubated for one minute at room temperature. Horseradish peroxidase (25 µl, 0.03 units, in 0.1M Tris-HCl, pH 8.0) was added and chemiluminescence was measured for 1 second in an Optocomp I (MGM) luminometer either in the presence (+) or absence (−) of added superoxide dismutase (85 units).

Results

| AP concentration (mol/10 µL) | Superoxide Dismutase (85 units) | Relative light units (RLU) |
| --- | --- | --- |
| 0 | − | 917 |
| $8.6 \times 10^{-15}$ | − | $1.3 \times 10^5$ |
| 0 | + | 452 |
| $8.6 \times 10^{-15}$ | + | 1214 |

The results demonstrate that superoxide dismutase quenches the chemiluminescence generating reaction, again indicating that $H_2O_2$ is not the product that is involved in the chemiluminescent-generating reaction observed herein.

EXAMPLE 5

Peroxidase-Catalyzed Enhancement of AP-Mediated Indoxyl-Chemiluminescence and Comparison With Peroxidase/Isoluminol/$H_2O_2$ Generated Chemiluminescence The method provided herein, in which enzyme is determined by measuring chemiluminescence generated by the enzyme-catalyzed hydrolysis of indoxyl esters and enhanced by horseradish peroxidase (HRP), is compared with a method (see, e.g., EP 0 476 930 A1) in which enzyme is determined by measuring the amount of $H_2O_2$ formed in the hydrolysis reaction using chemiluminesence systems, such as HRP/isoluminol or microperoxidase/isoluminol. Addition of SOD to the peroxidase/isoluminol-generated chemiluminescence (EXAMPLE 6) has no effect; whereas addition of SOD to the reactions run in accord with the methods herein, substantially quenches chemiluminescence (see, e.g., Examples 2 and 10).

A. Materials (1) Substrate reagents (a) 3.5 mM 3-indoxyl phosphate, di-(2-amino-2-methyl-1,3-propanediol salt (JBL, CA)) and 5 U/mL HRP in 0.1M diethanolamine buffer containing 2 mM $MgCl_2$, pH 10.

(b) 3.5 mM 3-indoxyl phosphate, di-(2-amino-2-methyl-1,3-propanediol salt (JBL, CA)) and 5 U/mL HRP in 0.1M diethanolamine buffer containing 2 mM $MgCl_2$ and 0.25 mM isoluminol, pH 10.

(2) Enzymes

AP was prepared in 0.1M diethanolamine+2mM $MgCl_2$ buffer, pH 10.0.

B. Method (a) 10 µL of the sample solutions (blank and alkaline phosphatase) were added to plastic tubes.

(b) 50 µL of each of the above substrate solutions was injected by the AccuLyte luminometer (LTI, IL) into the sample tubes.

(c) The sample tubes were incubated for one or fifteen minutes at room temperature.

(d) Chemiluminescence was measured using the AccuLyte luminometer for 5 seconds.

C. Results

| | Relative Light Units (RLU) | | | |
|---|---|---|---|---|
| Substrate | Blank | 100 pg AP a | Blank b | 100 pg AP |
| One minute incubation | 1144 | 492,048 | 1319 | $1.3 \times 10^6$ |
| Fifteen minutes incubation | 1459 | 331,330 | 1188 | 474,404 |

D. Discussion

The results show the differences between the HRP enhanced (no isoluminol) and the HRP/isoluminol/$H_2O_2$-generated chemiluminescence. The chemiluminescence produced from $H_2O_2$ by HRP/isoluminol/$H_2O_2$-generated one minute incubation exhibits a greater signal to noise ratio than the instant method, and chemiluminescence kinetics are different. There is a 32.7% reduction in signal using the HRP enhanced system compared to 63.5% using the HRP/isoluminol/$H_2O_2$. In addition, as demonstrated above, SOD, which converts the superoxide anion to $H_2O_2$ quenches the chemiluminescence produced in the reactions measured by the instant method; whereas, the chemiluminescence measured using peroxidase/isoluminol apparently is not quenched by SOD (see, e.g., Example 6). Thus, the instant methods detect an intermediate product.

EXAMPLE 6

SOD Does Not Quench Peroxidase/Isoluminol/$H_2O_2$-Generated Chemiluminescence

A. Materials (a) 3.5 mM 3-indoxyl phosphate, di-(2-amino-2-methylol, 3-propanediol salt (JBL, CA) 0.1M diethanolamine buffer containing 2 mM $MgCl_2$, pH 10.

(b) 0.38 mM 5 bromo-4-chloro-3 indoxyl phosphate, mono-(p-toluidinium) salt (JBL, CA) in 0.1M tris buffer containing 100 mM $MgCl_2$ (pH 9.5) and 0.1% bovine serum albumin.

(c) 0.12 mM isoluminol and 0.5 µM microperoxidase in 0.1M Tris containing 100 mM $MgCl_2$ and 0.1% BSA pH 9.6.

B. Method (1) Pipet 10 µL of blank and alkaline phosphatase solution into plastic tubes.

(2) Pipet 10 µL of 58 mU of SOD or zero mU (blank) of SOD to appropriate tubes.

(3) Add 100 µL of substrate solution (b, see materials).

(4) Incubate for one hour at 37° C.

(5) Inject 500 µL of the chemiluminescence reagent (see c above) into the AccuLyte luminometer.

(6) Measure chemiluminescence for 6 seconds interval from 15–21 seconds after the addition of 500 µL of (c) above (step #5) using the AccuLyte luminometer.

C. Results

| | Blank | 100 pg AP | Blank | 100 pg AP |
|---|---|---|---|---|
| SOD | None (0) | None (0) | 58 mU | 58 mU |
| RLU | 102,913 | $1.4 \times 10^7$ | 95,998 | $1.65 \times 10^7$ |

D. Discussion

The addition of SOD does not quench chemiluminescence, indicating that this system is based on determination of hydrogen peroxide.

EXAMPLE 7

Chemiluminescence Using Other Reagents

Materials (1) Alkaline phosphatase (AP) solution, $8.6 \times 10^{-15}$ mol/10 µL in 0.1M diethanolamine buffer containing 2 mM magnesium chloride ($MgCl_2$), pH 10.0, was prepared.

(2) Substrate solutions:

I. 2.3 mM 3-indoxyl phosphate, di-p-toludine salt in 70 mM diethanolamine buffer, pH 10.0, containing 2 mM $MgCl_2$ and 1.3 mM lucigenin.

II. 2.3 mM 3-indoxyl phosphate, di-p-toludine salt in 70 mM diethanolamine buffer, pH 10.0, containing 2 mM $MgCl_2$ and 1.3 mM luminol.

III. 2.3 mM 3-indoxyl phosphate, di-p-toludine salt in 70 mM diethanolamine buffer, pH 10.0, containing 2 mM $MgCl_2$ and 1.3 mM 2-methyl-6-[p-[2-[sodium 3-carboxylato-4-(6-hydroxy-3-xanthenon-9-yl] phenylthioureylene] ethyleneoxy]phenyl]-3,7-dihyroimidazo[1,2-α] pyrazin-3-one.

IV. 2.3 mM 3-indoxyl phosphate, di-p-toludine salt in 70 mM diethanolamine buffer, pH 10.0, containing 2 mM $MgCl_2$ and 1.3 mM 2-methyl-6-phenyl]-3,7-dihyroimidazo [1,2-α] pyrazin-3-one.

V. 2.3 mM 3-indoxyl phosphate, di-p-toludine salt in 70 mM diethanolamine buffer, pH 10.0, containing 2 mM $MgCl_2$ and 1.3 mM 7-dimethylamino-naphthalene- 1,2-dicarbonic acid hydrazide.

Methods

The alkaline phosphatase solution (10 µL) was introduced into a plastic tube. Substrate solution (10 µL) was added and chemiluminescence was measured in an OPTOCOMP1 (MGM) Luminometer for 6 seconds for 10 intervals.

Results

| SUBSTRATE | AP CONCENTRATION | INTERVAL | RELATIVE LIGHT UNITS (RLU) |
|---|---|---|---|
| I | Blank | 1 | 1374 |
| I | Blank | 2 | 1285 |
| I | Blank | 3 | 1239 |
| I | Blank | 4 | 1202 |
| I | Blank | 5 | 1187 |
| I | Blank | 6 | 1163 |
| I | $8.6 \times 10^{-15}$ mol | 1 | $9.8 \times 10^6$ |
| I | $8.6 \times 10^{-15}$ mol | 2 | $11.7 \times 10^6$ |
| I | $8.6 \times 10^{-15}$ mol | 3 | $12.3 \times 10^6$ |
| I | $8.6 \times 10^{-15}$ mol | 4 | $12.6 \times 10^6$ |
| I | $8.6 \times 10^{-15}$ mol | 5 | $12.6 \times 10^6$ |
| I | $8.6 \times 10^{-15}$ mol | 6 | $12.6 \times 10^6$ |
| II | Blank | 1 | 670 |

-continued

| SUB-STRATE | AP CONCENTRATION | INTERVAL | RELATIVE LIGHT UNITS (RLU) |
|---|---|---|---|
| II | Blank | 2 | 526 |
| II | Blank | 3 | 455 |
| II | Blank | 4 | 421 |
| II | Blank | 5 | 380 |
| II | Blank | 6 | 367 |
| II | $8.6 \times 10^{-15}$ mol | 1 | 1526 |
| II | $8.6 \times 10^{-15}$ mol | 2 | 12059 |
| II | $8.6 \times 10^{-15}$ mol | 3 | 9210 |
| II | $8.6 \times 10^{-15}$ mol | 4 | 8183 |
| II | $8.6 \times 10^{-15}$ mol | 5 | 8511 |
| II | $8.6 \times 10^{-15}$ mol | 6 | 8583 |
| III | Blank | 1 | 1498 |
| III | Blank | 2 | 1389 |
| III | Blank | 3 | 1370 |
| III | Blank | 4 | 1339 |
| III | Blank | 5 | 1323 |
| III | Blank | 6 | 1335 |
| III | Blank | 1 | 10327 |
| III | $8.6 \times 10^{-15}$ mol | 2 | 24731 |
| III | $8.6 \times 10^{-15}$ mol | 3 | 22402 |
| III | $8.6 \times 10^{-15}$ mol | 4 | 22598 |
| III | $8.6 \times 10^{-15}$ mol | 5 | 22699 |
| III | $8.6 \times 10^{-15}$ mol | 6 | 22258 |
| IV | Blank | 1 | 15209 |
| IV | Blank | 2 | 15879 |
| IV | Blank | 3 | 16569 |
| IV | Blank | 4 | 17198 |
| IV | Blank | 5 | 17618 |
| IV | Blank | 6 | 18024 |
| IV | $8.6 \times 10^{-15}$ mol | 1 | 103119 |
| IV | $8.6 \times 10^{-15}$ mol | 2 | 373120 |
| IV | $8.6 \times 10^{-15}$ mol | 3 | 268622 |
| IV | $8.6 \times 10^{-15}$ mol | 4 | 259158 |
| IV | $8.6 \times 10^{-15}$ mol | 5 | 257963 |
| IV | $8.6 \times 10^{-15}$ mol | 6 | 254675 |
| V | Blank | 1 | 500 |
| V | Blank | 2 | 410 |
| V | Blank | 3 | 361 |
| V | Blank | 4 | 338 |
| V | Blank | 5 | 313 |
| V | Blank | 6 | 293 |
| V | $8.6 \times 10^{-15}$ mol | 1 | 1618 |
| V | $8.6 \times 10^{-15}$ mol | 2 | 7063 |
| V | $8.6 \times 10^{-15}$ mol | 3 | 4430 |
| V | $8.6 \times 10^{-15}$ mol | 4 | 4054 |
| V | $8.6 \times 10^{-15}$ mol | 5 | 4075 |
| V | $8.6 \times 10^{-15}$ mol | 6 | 4104 |

EXAMPLE 8

Lucigenin-Augmented Chemiluminescence

Materials (1) Alkaline phosphatase (AP) solutions, $8.6 \times 10^{-15}$ mol/10 µL, $8.6 \times 10^{-17}$ mol/10 µL, and $8.6 \times 10^{-18}$ mol/10 µL, in 0.1M diethanolamine buffer containing 2 mM magnesium chloride ($MgCl_2$), pH 10.0, were prepared.

(2) Substrate solution 2.3 mM 3-indoxyl phosphate, di-p-toludine salt in 70 mM diethanolamine buffer, pH 10.0, containing 2 mM $MgCl_2$ and 1.3 mM lucigenin.

Methods

The alkaline phosphatase solution (10 µL) was introduced into a plastic tube. Substrate solution (10 µL) was added and chemiluminescence was measured in an OPTOCOMP1 (MGM) Luminometer for 20 second intervals for 20 intervals.

Results

| | RELATIVE LIGHT UNITS | | | |
|---|---|---|---|---|
| INTERVALS (20 seconds) | BLANK | $8.6 \times 10^{-15}$ mol AP | $8.6 \times 10^{-17}$ mol AP | $8.6 \times 10^{-18}$ mol AP |
| 1 | 1608 | $2.061 \times 10^{+7}$ | 107992 | 5972 |
| 2 | 1591 | $2.4092 \times 10^{+7}$ | 281509 | 10189 |
| 3 | 1611 | $2.4525 \times 10^{+7}$ | 412776 | 15918 |
| 4 | 1609 | $2.4201 \times 10^{+7}$ | 489377 | 20684 |
| 5 | 1607 | $2.3439 \times 10^{+7}$ | 531514 | 23830 |
| 6 | 1603 | $2.2398 \times 10^{+7}$ | 554319 | 25947 |
| 7 | 1579 | $2.1175 \times 10^{+7}$ | 567414 | 26842 |
| 8 | 1570 | $1.9814 \times 10^{+7}$ | 574907 | 27451 |
| 9 | 1546 | $1.8295 \times 10^{+7}$ | 580116 | 27562 |
| 10 | 1535 | $1.6813 \times 10^{+7}$ | 583030 | 27389 |
| 11 | 1547 | $1.54 \times 10^{+7}$ | 586353 | 27261 |
| 12 | 1535 | $1.41 \times 10^{+7}$ | 588084 | 26835 |
| 13 | 1521 | $1.29 \times 10^{+7}$ | 589354 | 26382 |
| 14 | 1515 | $1.19 \times 10^{+7}$ | 590844 | 25976 |
| 15 | 1464 | $1.10 \times 10^{+7}$ | 591703 | 25512 |
| 16 | 1476 | $1.03 \times 10^{+7}$ | 592857 | 25092 |
| 17 | 1440 | $.96 \times 10^{+7}$ | 593530 | 24687 |
| 18 | 1438 | $.90 \times 10^{+7}$ | 592865 | 24145 |

-continued

| INTERVALS | | RELATIVE LIGHT UNITS | | |
|---|---|---|---|---|
| (20 seconds) | BLANK | $8.6 \times 10^{-15}$ mol AP | $8.6 \times 10^{-17}$ mol AP | $8.6 \times 10^{-18}$ mol AP |
| 19 | 1425 | $.85 \times 10^{+7}$ | 593054 | 24000 |
| 20 | 1420 | $.81 \times 10^{+7}$ | 592819 | 23437 |

EXAMPLE 9

Effect of Superoxide Dismutase on Indoxyl-Lucigenin Generated Chemiluminescence

Materials

Substrate solution containing 3-indoxyl phosphate toluidine salt (2.3 mM) lucigenin (1.3 mM) in diethanolamine buffer (70 mM; $MgCl_2$ (2.0 mM); pH 10.0).

Methods

Substrate solution was added to 10 μL of alkaline phosphatase ($8.6 \times 10^{-15}$ mol) sample, and incubated for one minute at room temperature. After the minute incubation either nothing (−) was added or 85 units of superoxide dismutase (+) was added, and chemiluminescence was measured for 1 sec in the Optocomp I (MGM) luminometer.

Results

| AP concentration (mol/10 μL) | Superoxide Dismutase (85 units) | Relative light units (RLU) |
|---|---|---|
| 0 | − | 1457 |
| $8.6 \times 10^{-15}$ | − | $1.1 \times 10^6$ |
| 0 | + | 1824 |
| $8.6 \times 10^{-15}$ | + | 6371 |

The results demonstrate that superoxide dismutase quenches the chemiluminescence generating reaction, thereby, suggesting that superoxide anion, not $H_2O_2$, is involved in the chemiluminescence that is observed in these reactions.

EXAMPLE 10

Effect of SOD on Lucigenin-Amplified Chemiluminescence

A. Materials 3.5 mM 3-indoxyl phosphate, di-(2-amino-2-methylol, 3-propanediol salt (JBL, CA)) 0.1M diethanolamine buffer containing 2 mM $MgCl_2$, pH 10.

B. Method (1) Pipet 10 μL of blank and alkaline phosphatase solution into plastic tubes.

(2) Pipet 10 μL of 58 mU of SOD (prepared in the buffer used for AP or for the blank) or zero mU (blank) of SOD to appropriate tubes.

(3) Add 50 μL of 3.5 mM 3-indoxyl phosphate, di-(2-amino-2-methyl-1,3-propanediol salt (JBL, CA)) in 0.1M diethanolamine buffer containing 1.25 mM lucigenin and 2 mM $MgCl_2$, pH 10.

(4) Incubate for one minute and measure chemiluminescence for 1 second using the AccuLyte luminometer.

C. Results

| | Blank | 100 pg AP | Blank | 100 pg AP |
|---|---|---|---|---|
| SOD | None (0) | None (0) | 58 mU | 58 mU |
| RLU | 1836 | $2.0 \times 10^6$ | 1,550 | 86,931 |

D. Discussion

The above experiment demonstrates that approximately 96% of chemiluminescence is quenched. Thus, addition of SOD substantially quenches chemiluminescence, indicating that in the methods herein, $H_2O_2$ is not quantitated.

EXAMPLE 11

Two-Step Assay in Which the Hydrolysis Reaction Proceeds Before Addition of Any Amplifying Reagent and Effect of Increasing Enzyme Concentration

A. Method (1) Pipet 10 μL of blank and alkaline phosphatase solution into plastic tubes.

(2) Add 35 μL of 3.5 mM 3-indoxyl phosphate, di-(2-amino-2-methyl)-1,3-propanediol salt (JBL, CA) 0.1M diethanolamine buffer containing 2 mM $MgCl_2$, pH 10.

(3) Incubate for two minutes at room temperature.

(4) Inject 50 μL of 0.5 mM lucigenin in 0.1M 2-amino-2-methylpropanol (AMP) buffer into the mixture.

(5) Measure chemiluminescence for one second, using the AccuLyte luminometer.

B. Results

| AP (pg/10 μL) | RLU (1 sec) |
|---|---|
| 0 | 332 |
| 1 | 4,239 |
| 10 | 308,336 |
| 100 | $1.4 \times 10^6$ |

EXAMPLE 12

Comparison of the Lucigenin-Indoxyl Chemiluminescence System (Method 1) and Two-Step Lucigenin-Indoxyl System Based on Detection of $H_2O_2$ by Chemiluminescence (Method 2)

Materials

A. Reagents (1) 3.5 mM 3-indoxyl phoshate, di-(2-amino-2-methyl-1,3-propanediol salt (JBL, CA)) and 1.25 mM lucigenin in 70 mM M diethanolamine buffer containing 2 mM MgC12, pH 10.

(2) 0.38 mM 5 bromo-4-chloro-3 indoxyl phoshate, mono-(p-toluidinium) salt (JBL, CA)) in 0. 1M Tris buffer containing 100 mM MgC12 (pH 9.5). and 0.1% BSA (see, EP 0 476 930 A1)

(3) $6 \times 10^{-4}\%$ lucigenin in 0.1M KOH and $1 \times 10^{-3}$M Triton X-100 (see, Tsuji et al. in *Proc. J. International Symposium on Bioluminescence and Chemiluminescence*, Cambridge, 1990, Page 119).

(1) Method 1 (method described herein)

(a) Piper 10 μL of blank and alkaline phosphatase (prepared in 0.1M DEA buffer containing 2 mm $MgCl_2$, pH 10) into plastic tubes.

(b) add 25 μL of the reagent a and incubate for 4 minutes at 37° C.

(c) Measure chemiluminescence using the AccuLyte luminometer for 1 second.

Method 2 (prior art method)

(a) Pipet 10 μL of blank and alkaline phosphatase (prepared in the 0.1M Tris buffer containing 0.1% BSA and 100 mM $MgCl_2$, pH 9.5 (see, EP 0 476 930 A1) into plastic tubes.

(b) Add 100 μL of the substrate solution (reagent (2)) and incubate for one hour at 37° C.

(c) Inject 500 μL of reagent (3) using the AccuLyte luminometer.

(d) Measure chemiluminescence using the AccuLyte luminometer for 10 second interval from 15–25 seconds (Tsuji et al. in *Proc. J. International Symposium on Bioluminescence and Chemiluminescence*, Cambridge, 1990, Page 119).

C. Results

| AP | Method (1) (RLU) | S/N* | Method (2) (RLU) | S/N* |
|---|---|---|---|---|
| Blank (0) | 2429 | 1 | $1.9 \times 10^6$ | 1 |
| 100 pg AP | $6.1 \times 10^6$ | 2,511 | $3.3 \times 10^7$ | 17.4 |
| 10 pg AP | 534,405 | 220 | $3.6 \times 10^6$ | 1.9 |
| 1 pg | 48,199 | 19.8 | $2.0 \times 10^6$ | 1.1 |
| 0.1 pg | 4,586 | 1.9 | $1.8 \times 10^6$ | 0.95 |

*S/N = signal/noise
†signal ≈ background

D. Discussion

The methods of the prior art [see, e.g., EP 0 476 930 A1; and Tsuji et al. in *Proc. J. International Symposium on Bioluminescence and Chemiluminescence*, Cambridge, 1990, Page 119] measure $H_2O_2$ and, thus, employ lucigenin at relatively high pH.

The instant method, method 1, detects approximately 0.1 pg of alkaline phosphatase; whereas, method 2, which measures $H_2O_2$ detects about 10 pg. Thus, method 1 is about 100-fold more sensitive than method (2), which is based on $H_2O_2$.

EXAMPLE 13

Comparison of the Detection Limit of Method (1) and Method (2)

A. Materials (1) 3.5 mM 3-indoxyl phosphate, di-(2-amino-2-methyl-1,3-propanediol salt (JBL, CA)) and 1.25 mM lucigenin in 70 mM diethanolamine buffer containing 2 mM $MgCl_2$, pH 10.

(2) 0.38 mM 5-bromo-4-chloro-3-indoxyl phosphate, mono-(p-toluidinium) salt (JBL, CA)) in 0.1M tris buffer containing 100 mM $MgCl_2$ and 0.1% bovine serum albumin (pH 9.5) [see, EP 0 476 930 A1].

(3) 0.12 mM isoluminol and 0.5μM microperoxidase in 10 mM Tris containing 100 mM $MgCl_2$, pH 9.5.

B. Methods

Method (1)

(a) Pipet 10 μL of blank and alkaline phosphatase solution into plastic tubes.

(b) Add 50 μL of reagent (1).

(c) Incubate for three minutes at room temperature.

(d) Measure chemiluminescence for one second using the AccuLyte luminometer.

Method (2)

(a) Pipet 10 μL of blank and alkaline phosphatase solution into plastic tubes.

(b) Add 50 μL of reagent (2).

(c) Incubate for one hour at 37° C.

(d) Inject 500 μL of the chemiluminescence reagent (3) into the AccuLyte luminometer and measure chemiluminescence for 6 second intervals from 15–21 seconds after addition of reagent (3) using the AccuLyte luminometer.

C. Results*

| | Method (1) | Method (2) |
|---|---|---|
| Incubation time: | 3 minute at room temp | One hour at 37° C. |
| Detection limit: | 0.15 pg | 1.0 pg |

*Determinations were performed in ten replicates
Detection limit is defined as the quantity of alkaline phosphatase determined that is two standard deviations above the blank value.

D. Discussion

The detection limit achieved using the method herein (method (1)) is approximately seven times better than that achieved using method (2) (see, EP 0 476 930). This increase is achieved despite the combined effect of temperature (37° C.) and longer incubation (one hour) of method (2). Thus, the instant methods, in addition to providing greater sensitivity, (a) require much shorter (½0th) incubation times; (b) doe not require 37° C.; and (d) are simpler (one-step).

The two-step methods provided herein provide even higher sensitivity.

EXAMPLE 14

Comparison of the Lucigenin-Indoxyl Chemiluminescence Systems in Which Intermediates or Reactive Metabolites Are Determined With Lucigenin-Indoxyl Systems in Which $H_2O_2$ is Determined The method provided herein, in which enzyme is determined by measuring chemiluminescence generated by the enzyme-catalyzed hydrolysis of indoxyl esters and augmented by lucigenin, is compared with a method in which enzyme is determined by measuring the amount of $H_2O_2$ formed in the hydrolysis reaction using chemiluminesence systems in which lucigenin is used under conditions (see, Maeda, et al. (1990) "Chemiluminescent Assay of Alkaline Phosphatase Using Ascorbic Acid 2-Phosphate as Substrate and its Application to Chemiluminescent Enzyme Immunoassays," *Bioluminescence and Chemiluminescence*, pp. 119–122). under which is reacts with $H_2O_2$.

A. Materials (1) Reagents (a) 3-Indoxyl phosphate (2.5 mM), di-(2-amino-2-methyl)1, 3-propanediol salt (JBL, CA)) and 1.25 mM lucigenin in 70 mM diethanolamine buffer containing 2 mM $MgCl_2$, pH 10.

b) 5-Bromo-4 -chloro-3 indoxyl phosphate (0.19 mM), mono-(p-toluidinium) salt (JBL, CA)) in 0.01M Tris buffer containing 100 mM $MgCl_2$ (pH 9.5).

(c) Lucigenin ($6\times10^{-4}$%) in 0.1M KOH and $1\times10^{-3}$M Triton X-100 (see, Tsuji et al in *Proc. J. International Symposium on Bioluminescence and Chemiluminescence*, Cambridge, 1990, Page 119).

B. Methods (1) lucigenin-augmented chemiluminescence (a) Pipet 10 μL of blank and alkaline phosphatase into plastic tubes.

(b) Add 50 μL of the reagent a.

(c) Incubate for two minutes inside the luminometer.

(e) Measure chemiluminescence using the AccuLyte luminometer for 1 second.

(2) $H_2O_2$ based chemiluminescence assay (a) Pipet 10 μL of blank and alkaline phosphatase (prepared in the 0.1M Tris buffer containing 0.1% BSA and 100 mM $MgCl_2$ (pH 9.5) into plastic tubes.

(b) Add 200 μl of the substrate solution (reagent b).

(c) Inject 500 μL of reagent c into the AccuLyte luminometer.

(d) Incubate for two minutes inside the luminometer.

(e) Measure chemiluminescence using the AccuLyte luminometer for 1 second.

C. Results

|  | Method (1) | | Method (2) | |
|---|---|---|---|---|
|  | RLU | S/N | RLU | S/N |
| Blank (0) | 2275 | 1 | $1.5 \times 10^6$ | 1 |
| 100 pg AP | $2.45 \times 10^6$ | 1076.9 | $1.3 \times 10^7$ | 8.7 |
| 10 pg AP | 165,916 | 72.9 | $1.4 \times 10^6$ | 0 |
| 1 pg | 4241 | 1.86 | $1.2 \times 10^6$ | 0.8 |

Note: S/N = signal/noise

D. Discussion

The sensitivity achieved using the two systems is remarkably different. When 1 pg of alkaline phosphatase was added, the S/N in method (1) was 1.8; whereas, when 100 pg was added the S/N in method (2) was 8.7, indicating that method (1) has higher sensitivity.

EXAMPLE 15

Assay for Prostate Specific Antigen

Materials (1) Immuno enzymometric assay for prostrate specific antigen (AIA-PACK PA catalog no. 020263 TOSOH). The AIA-PACK PA is a two-site immunoenzymmometric assay in which mouse anti-prostate-specific antigen (abbreviated PSA or PA) is immobilized on paramagnetic particles and the second antibody, which is anti-human PA monoclonal antibody, is conjugated to intestinal alkaline phosphatase.

(2) Substrate 2.3 mM 3-indolyl phosphate di-p-toluidine salt (Diagnostic Chemical Labs (DCL), Canada) and 1.3 mM lucigenin in 70 mM diethanolamine buffer containing 2.0 mM magnesium chloride, pH 10.0.

Methods

The alkaline phosphatase-conjugated antibody and the coated paramagnetic beads were introduced into plastic tubes. 100 μL of the diluent solution (provided with the kit) was added, and the resulting mixture was vortexed. PSA calibrator solution (20 μl; provided in the kit) or BIO-RAD Lyphocheck Immunoassay controls, levels 1, 2, and 3 (20 μl; obtained from Bio-Rad, CA, lot#s 92001, 92002, 92003, respectively) were added. The tubes were incubated for 20 minutes, the beads were washed four times with 0.5 ml wash solution (provided in the kit) and then two times with distilled water.

Substrate solution (100 μL) was then added and the resulting mixture was incubated for 4 minutes. Chemiluminescence was measured in a Berthold luminometer, Model #952. The chemiluminescent output was measured for 1 second.

Results

The data from the calibrators was used to generate a standard dose-response curve. The concentrations of the BIO-RAD lyphochek controls were then determined from this standard dose-response curve. As shown in the following Table, the results obtained using the methods herein accurately determined the concentrations of the PSA in the Bio-Rad Lyphochek controls.

| Samples | Relative light units (RLU)* | Concentration ratio (ng/ml)** | Reported concentration range (ng/ml)*** |
|---|---|---|---|
| Standards | | | |
| 1 | 1276 | 0.0 | — |
| 2**** | 8995 | 5.200 | — |
| 3**** | 29372 | 25.800 | — |
| 4 | 90555 | 51.600 | — |

-continued

| Samples | Relative light units (RLU)* | Concentration ratio (ng/ml)** | Reported concentration range (ng/ml)*** |
|---|---|---|---|
| BIO-RAD | | | |
| 1 | 3499 | 1.409 | 0.8–1.5 |
| 2 | 4540 | 2.057 | 2.8–4.0 |
| 3 | 34594 | 28.474 | 22.1–32.1 |

*Mean value from two samples
**determined from standard curve generated using the standards
***as reported in the Bio-Rad package insert provided with the Lypocheck controls (lot no. 92001, level 1; 92002, level 2; and 92003, level 3)

EXAMPLE 16

Assay for β-Galactosidase

Materials

β-galactosidase (Boehringer Mannheim, Germany).

AMPSO buffer (3-[1,1-dimethyl-2-hydroxyethyl]amino]-2-hydroxypropanesulfonic acid; SIGMA Chemical Company).

Substrate solution is 1.6 mM 5-bromo-4-chloro-3-O-indolyl-β-D-galactopyranoside (Diagnositic Chemicals LTD, Canada) and 1.3 mM lucigenin in 0.1M AMPSO buffer, pH 8.9.

Methods

β-galactosidase (10 μL of varying concentrations) in 0.1M AMPSO buffer and 0.1% TRITON X-100, pH 8.9 was mixed with 100 μl of substrate solution. The resulting mixture was incubated for 3 minutes at room temperature. Chemiluminescence was immediately measured in an MGM OPTOCOMP I tube luminometer. The chemiluminescent output was measured for 1 second.

Results

| Concentration Enzyme (mol/10 μl) | Relative light units (RLU) |
|---|---|
| 0 | 284 |
| $9 \times 10^{-13}$ | 481342 |
| $9 \times 10^{-15}$ | 4559 |

Since modifications will be apparent to those of skill in this art, it is intended that this invention be limited only by the scope of the appended claims.

I claim:

1. A method for determining enzyme activity in a sample comprising:

combining the sample with a substrate selected from indoxyl ester, thioindoxyl ester and benzofuran ester to produce a hydrolysis product upstream of $H_2O_2$ production;

reacting the hydrolysis product upstream of $H_2O_2$ production with a chemiluminescence generating reagent to produce chemiluminescence;

measuring the chemiluminescence produced; and correlating the chemiluminescence measured with the enzyme activity in the sample.

2. The method of claim 1 wherein the indoxyl ester is a 3-O-indoxyl ester having the formula:

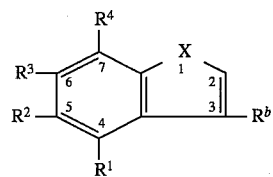

wherein O, S or $NR^a$, in which $R^a$ is hydrogen, halogen, alkyl, alkoxy, alkoxyalkyl, aryl, aryloxy, hydroxyl, carboxyl, carboxyl lower alkoxy, aryloxycarbonyl, arylcarbonyl lower alkoxy, nitro, acyl or lower acylamino groups, in which the lower alkyl groups contain from 1 to 6 carbons, and the aryl groups contain from 4 to 7 members;

wherein $R^b$ is hydrolyzed by the enzyme; and wherein $R_1$, $R_2$, $R_3$ and $R_4$ are independently selected from the group of hydrogen, halide, pseudohalide, haloalkyl, alkylamino, hydroxyl, alkyl, alkoxyalkyl, amino, in which the alkyl groups contain from 1 to 6 carbons.

3. The method of claim 2 wherein at least one of $R_1$, $R_2$, $R_3$ and $R_4$ is selected from the group consisting of cyano, amino, amino substituted with 1 or 2 methyl or ethyl groups, trihalomethyl, hydroxyl, halide, methyl, ethyl, methoxy and ethoxy.

4. The method of claim 2 wherein at least two of $R_1$, $R_2$, $R_3$ and $R_4$ is hydrogen and at least one of $R_1$, $R_2$, $R_3$ and $R_4$ is halide.

5. The method of claim 2 wherein $R^b$ is selected from the group consisting of phosphate, acetate, galactopyranoside, sulfate, glucuronate, glucopyranoside, fructopyranoside, mannopyranoside.

6. The method of claim 1 wherein the enzyme is selected from the group consisting of alkaline phosphatases, sulfatases, proteases and galactosidases.

7. The method as in one of claims 1–6 wherein the hydrolysis product upstream of $H_2O_2$ production is selected from the group of superoxide anion $O_2^-$ and indoxyl radicals.

8. The method as in one of claims 1–6 wherein the chemiluminescent generating reagent is selected from the group of horseradish peroxidase, Lucigenin, 7-dimethylamino-naphthalene-1,2-dicarbonic acid hydrazine, 2-methyl-6-[p-methoxyphenyl]-3, 7-dihiroimidazo[1,2-α] pyrazin-3-one, 2-methyl-6-phenyl]-3,7-dihiroimidazo[1,2-α] pyrazin-3-one, 2-methyl-6-[p-[2-[sodium 3-carboxylato-4-(6-hydroxy-3-xanthenon-9-yl] phenylthioureylene]-ethyleneoxy] phenyl]-3,7-dihiroimidazo[1,2-α] pyrazin-3-one.

9. The method as in one of claims 1–6 further comprising reacting the hydrolysis product upstream of $H_2O_2$ production with a chemiluminescence amplifying reagent.

10. The method as in one of claims 1–6 further comprising reacting the hydrolysis product upstream of $H_2O_2$ production with a chemiluminescence amplifying reagent selected from the group of peroxidase, phophasin and Lucigenin.

11. A method for determining enzyme activity in a sample, comprising:

combining the sample with a benzofuran ester to produce a hydrolysis intermediate other than $H_2O_2$ which is chemiluminsescent; and measuring the chemiluminescence produced from the hydrolysis intermediate other than $H_2O_2$; and correlating the chemiluminescence measured with the enzyme activity in the sample.

12. The method of claim 11 wherein the hydrolysis intermediate other than $H_2O_2$ is an intermediate compound in the formation of an indigo dye.

13. The method of claim 11 wherein the indoxyl ester is a 3-O-indoxyl ester having the formula:

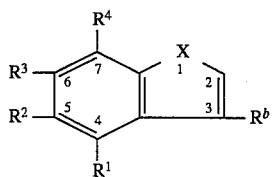

wherein X is O, S or NR$^a$, in which R$^a$ is hydrogen, halogen, alkyl, alkoxy, alkoxyalkyl, aryl, aryloxy, hydroxyl, carboxyl, carboxyl lower alkoxy, aryloxycarbonyl, arylcarbonyl lower alkoxy, nitro, acyl or lower acylamino groups, in which the lower alkyl groups contain from 1 to 6 carbons, and the aryl groups contain from 4 to 7 members;

wherein R$^b$ is hydrolyzed by the enzyme; and wherein $R_1$, $R_2$, $R_3$ and $R_4$ are independently selected from the group of hydrogen, halide, pseudohalide, haloalkyl, alkylamino, hydroxyl, alkyl, alkoxyalkyl, amino, in which the alkyl groups contain from 1 to 6 carbons.

14. The method of claim 13 wherein at least one of $R_1$, $R_2$, $R_3$ and $R_4$ is selected from the group consisting of cyano, amino, amino substituted with 1 or 2 methyl or ethyl groups, trihalomethyl, hydroxyl, halide, methyl, ethyl, methoxy and ethoxy.

15. The method of claim 13 wherein at least two of $R_1$, $R_2$, $R_3$ and $R_4$ is hydrogen and at least one of $R_1$, $R_2$, $R_3$ and $R_4$ is halide.

16. The method of claim 13 wherein R$^b$ is selected from the group consisting of phosphate, acetate, galactopyranoside, sulfate, glucuronate, glucopyranoside, fructopyranoside, mannopyranoside.

17. The method of claim 11 wherein the enzyme is selected from the group consisting of alkaline phosphatases, sulfatases, proteases and galactosidases.

18. The method as in one of claims 11–17 further comprising reacting the hydrolysis intermediate other than $H_2O_2$ with a chemiluminescence amplifying reagent.

19. The method as in one of claims 11–17 further comprising reacting the hydrolysis intermediate other than $H_2O_2$ with a chemiluminescence amplifying reagent selected from the group of peroxidase, phophasin and Lucigenin.

20. A method for determining enzyme activity in a sample, comprising:

combining the sample with a substrate selected from indoxyl ester, thioindoxyl ester and benzofuran ester to produce a hydrolysis product other than $H_2O_2$;

reacting the hydrolysis product other than $H_2O_2$ with a chemiluminescence generating reagent to produce chemiluminescence;

measuring the chemiluminescence produced; and correlating the chemiluminescence measured with the enzyme activity in the sample.

* * * * *